United States Patent
Dove

(10) Patent No.: US 11,872,355 B2
(45) Date of Patent: Jan. 16, 2024

(54) MEDICAL DEVICE FOR DETECTING FLUID PARAMETERS USING FLUORESCENT PROBES

(71) Applicant: Covidien LP, Mansfield, MA (US)

(72) Inventor: Jacob D. Dove, Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 344 days.

(21) Appl. No.: 17/013,294

(22) Filed: Sep. 4, 2020

(65) Prior Publication Data

US 2022/0072273 A1 Mar. 10, 2022

(51) Int. Cl.
- A61B 5/00 (2006.01)
- A61M 25/01 (2006.01)
- A61K 49/04 (2006.01)
- A61K 49/00 (2006.01)

(52) U.S. Cl.
CPC ....... *A61M 25/0105* (2013.01); *A61B 5/0071* (2013.01); *A61K 49/0017* (2013.01); *A61K 49/0419* (2013.01); *A61M 2025/0166* (2013.01); *A61M 2202/0007* (2013.01); *A61M 2202/0208* (2013.01); *A61M 2202/0496* (2013.01); *A61M 2205/3334* (2013.01); *A61M 2205/587* (2013.01); *A61M 2210/1085* (2013.01)

(58) Field of Classification Search
CPC ...... A61M 25/0105; A61M 2025/0166; A61M 2202/0007; A61M 2202/0208; A61M 2202/0496; A61M 2205/3334; A61M 2205/587; A61M 2210/1085; A61B 5/0071; A61B 5/6852; A61B 5/20; A61K 49/0017; A61K 49/0419
See application file for complete search history.

(56) References Cited

U.S. PATENT DOCUMENTS

| | | | |
|---|---|---|---|
| 5,713,364 A * | 2/1998 | DeBaryshe | G01N 21/4795 600/407 |
| 5,773,835 A | 6/1998 | Sinofsky | |
| 6,201,989 B1 * | 3/2001 | Whitehead | A61B 5/6848 250/461.2 |
| 6,352,502 B1 * | 3/2002 | Chaiken | G01N 21/65 600/475 |
| 6,379,969 B1 | 4/2002 | Mauze et al. | |
| 7,181,096 B2 | 2/2007 | Matsumoto et al. | |
| 8,553,649 B2 | 10/2013 | Zhang et al. | |

(Continued)

FOREIGN PATENT DOCUMENTS

| WO | 2019/143676 A1 | 7/2019 |
|---|---|---|
| WO | 2020/006549 A1 | 1/2020 |

OTHER PUBLICATIONS

Office Action from U.S. Appl. No. 17/168,935 dated Nov. 25, 2022, 9 pp.

(Continued)

*Primary Examiner* — May A Abouelela
(74) *Attorney, Agent, or Firm* — Fletcher Yoder, P.C.

(57) ABSTRACT

An example device includes an elongated body defining a lumen, the elongated body comprising a proximal portion and a distal portion; and one or more sensors configured to: stimulate a fluorescence response from one or more fluorescent probes released into a fluid and flowing with the fluid through the lumen; and detect the fluorescence response, wherein the fluorescence response is indicative of a composition of the fluid.

23 Claims, 9 Drawing Sheets

(56) References Cited

U.S. PATENT DOCUMENTS

| | | | |
|---|---|---|---|
| 8,649,836 | B2 | 2/2014 | Shimizu et al. |
| 8,715,254 | B2 | 5/2014 | Nishtala |
| 8,848,188 | B2 | 9/2014 | Nishino et al. |
| 9,737,213 | B1* | 8/2017 | Heaton, II ......... A61B 5/14552 |
| 9,848,787 | B2 | 12/2017 | White et al. |
| 10,398,365 | B2 | 9/2019 | Takahashi et al. |
| 10,631,746 | B2* | 4/2020 | Flower ................. A61B 5/0275 |
| 10,632,247 | B1* | 4/2020 | Woods .................. A61M 25/10 |
| 2004/0186351 | A1* | 9/2004 | Imaizumi ............. A61B 1/046 600/476 |
| 2007/0263210 | A1 | 11/2007 | Taguchi et al. |
| 2009/0054908 | A1* | 2/2009 | Zand ................... A61B 5/7275 600/300 |
| 2012/0029328 | A1* | 2/2012 | Shimizu ............. A61B 5/14532 600/316 |
| 2013/0109963 | A1* | 5/2013 | Zhu ...................... A61B 5/0091 600/427 |
| 2014/0114150 | A1* | 4/2014 | Pogue .................. A61N 5/1075 600/323 |
| 2014/0276034 | A1* | 9/2014 | Eggers ................. A61B 5/0071 424/9.1 |
| 2015/0282749 | A1* | 10/2015 | Zand .................... A61B 5/0084 600/301 |
| 2016/0157722 | A1* | 6/2016 | Kubo ...................... G06T 19/20 600/476 |
| 2018/0052093 | A1* | 2/2018 | Shi .......................... B01F 33/30 |
| 2018/0199829 | A1 | 7/2018 | White et al. |
| 2018/0318452 | A1* | 11/2018 | Thompson ......... A61K 49/0021 |
| 2019/0069831 | A1* | 3/2019 | Kuck ..................... A61B 5/208 |
| 2019/0086316 | A1 | 3/2019 | Rice et al. |
| 2019/0099584 | A1* | 4/2019 | Erbey, II ............. A61M 27/008 |
| 2019/0110686 | A1* | 4/2019 | Kato .................... A61B 5/0071 |
| 2019/0150801 | A1 | 5/2019 | Suehara et al. |
| 2019/0343445 | A1* | 11/2019 | Burnett ............. A61M 25/0068 |
| 2020/0022636 | A1 | 1/2020 | Suehara et al. |
| 2020/0022638 | A1 | 1/2020 | Suehara et al. |
| 2020/0046943 | A1* | 2/2020 | Vunjak-Novakovic ...................... A61M 25/0905 |
| 2020/0054800 | A1* | 2/2020 | Wilbourn .......... A61M 25/0017 |
| 2020/0064172 | A1 | 2/2020 | Tabaczewski et al. |
| 2020/0158548 | A1 | 5/2020 | Rice et al. |
| 2020/0234439 | A1* | 7/2020 | Chang .............. A61B 1/000095 |
| 2020/0281503 | A1* | 9/2020 | Salamini ................ A61B 6/481 |
| 2020/0367722 | A1* | 11/2020 | Perez-Lizano ....... A61B 1/0051 |
| 2021/0228066 | A1* | 7/2021 | Liu ..................... A61B 1/00188 |
| 2021/0236005 | A1* | 8/2021 | Gebicki ............... A61B 5/0261 |
| 2021/0302314 | A1* | 9/2021 | Kawada .................. A61B 1/00 |
| 2022/0015676 | A1* | 1/2022 | Miller ...................... A61B 5/20 |
| 2022/0079697 | A1* | 3/2022 | Sato ........................ A61B 90/36 |

OTHER PUBLICATIONS

Mahoney et al., "Review—Point-of-Care Urinalysis with Emerging Sensing and Imaging Technologies", ECS, Journal of the Electrochemical Society, vol. 167, Dec. 11, 2019, 15 pp.

Nawrot et al., "A Fluorescent Biosensors for Detection Vital Body Fluids' Agents", MDPI, Sensors, vol. 18, No. 8, doi:10.3390/s18082357, Jul. 24, 2018, 28 pp.

U.S. Appl. No. 17/168,935, filed Feb. 5, 2021, naming inventor Dove.

Wolfbeis, "Luminescent sensing and imaging of oxygen: Fierce competition to the Clark electrode," Methods, Models & Techniques, Prospects & Overviews, Bioessays 37: Jun. 2015, pp. 921-928.

U.S. Appl. No. 16/854,592, filed Apr. 21, 2020 naming inventor David J. Miller.

U.S. Appl. No. 63/075,001, filed Sep. 4, 2020 naming inventor Jacob D. Dove.

Labsphere, "Technical Guide: Integrating Sphere Uniform Light Source Applications," May 2008, 16 pp.

Final Office Action from U.S. Appl. No. 17/168,935 dated Jun. 8, 2023, 7 pp.

Response to Office Action dated Nov. 25, 2022 from U.S. Appl. No. 17/168,935, filed Feb. 27, 2023, 10 pp.

Advisory Action from U.S. Appl. No. 17/168,935 dated Sep. 14, 2023, 3 pp.

Response to Final Office Action dated Jun. 8, 2023 from U.S. Appl. No. 17/168,935, filed Aug. 7, 2023, 9 pp.

* cited by examiner

MEDICAL DEVICE FOR DETECTING FLUID PARAMETERS USING FLUORESCENT PROBES

TECHNICAL FIELD

This disclosure relates to medical devices, more particularly, to catheters.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter used for longer time periods than a non-Foley catheter. Some Foley catheters are constructed of silicon rubber and include an anchoring member, which may be an inflatable balloon inflated in a patient's bladder to serve as an anchor, so a proximal end of the catheter does not slip out of the patient's bladder.

SUMMARY

The disclosure describes catheters (e.g., a Foley catheter) and systems that sense one or more parameters of a fluid, such as oxygenation and/or flow rate of urine, flowing through the catheter by stimulating and measuring fluorescence of injected materials, such as microbeads suspended and/or dispersed in the fluid, and methods of making and using the catheters and systems.

In one example, this disclosure describes a device that includes an elongated body and one or more sensors. The elongated body defines a lumen and includes a proximal portion and a distal portion. The one or more sensors are configured to stimulate a fluorescence response from one or more fluorescent probes released into a fluid and flowing with the fluid through the lumen and detect the fluorescence response. The fluorescence response is indicative of a composition of the fluid.

In another example, this disclosure describes a method that includes injecting one or more fluorescent probes into a fluid flowing in a lumen defined by an elongated body comprising a proximal portion and a distal portion. The one or more fluorescent probes are configured to flow with the fluid in the lumen. The method further includes stimulating a fluorescence response from the one or more fluorescent probes in the fluid flowing through the lumen and detecting the fluorescence response. The fluorescence response is indicative of a composition of the fluid.

In another example, this disclosure describes a system that includes an elongated body defining a lumen, a plurality of fluorescent microbeads, and one or more sensors in photonic communication with the lumen. The elongated body includes a proximal portion and a distal portion. The plurality of fluorescent microbeads is configured to flow through the lumen and fluoresce in response to light. The one or more sensors are configured to stimulate a fluorescence response from the plurality of fluorescent microbeads in the fluid flowing through the lumen and detect the fluorescence response from the plurality of fluorescent microbeads. The fluorescence response is indicative of a composition of the fluid.

The details of one or more examples are set forth in the accompanying drawings and the description below. Other features, objects, and advantages will be apparent from the description and drawings, and from the claims.

DETAILED DESCRIPTION

Figure 1:
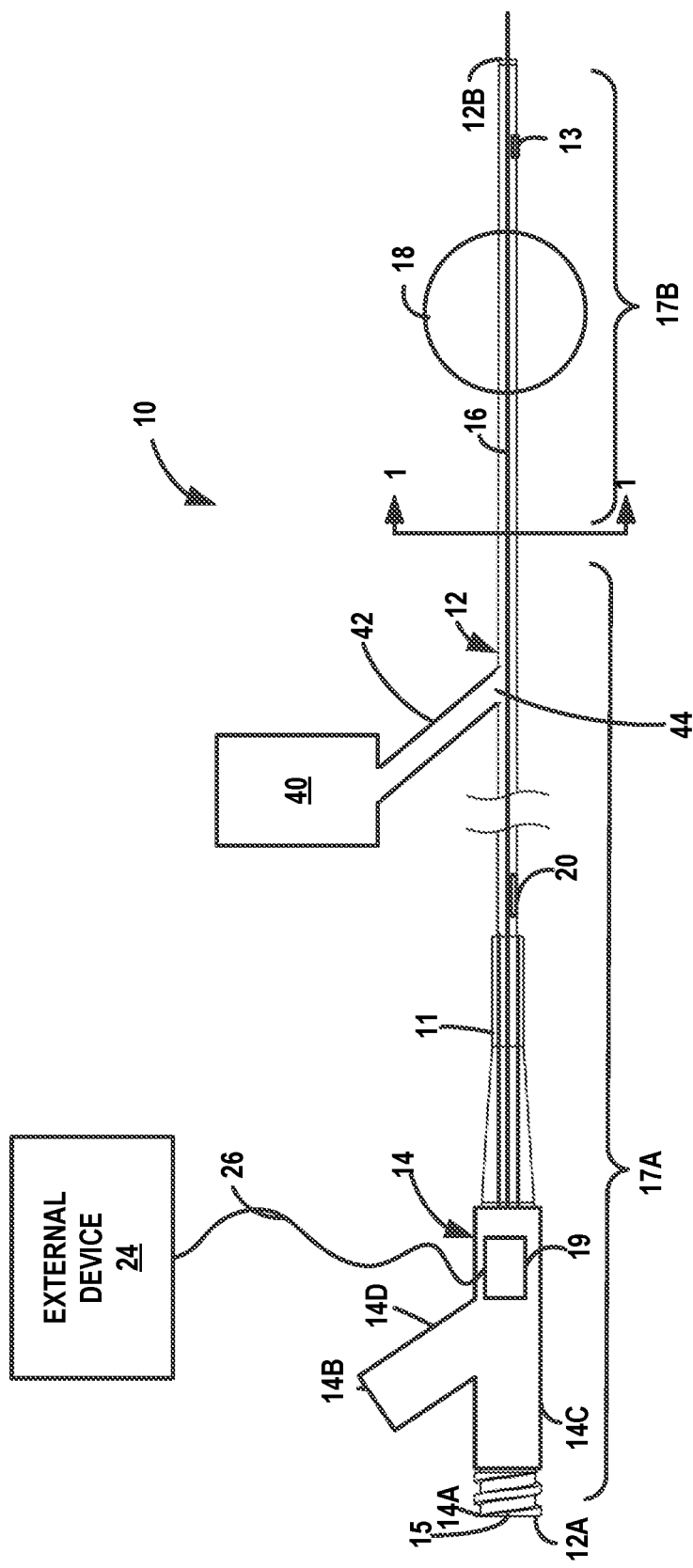
FIG. 1 is a diagram illustrating an example medical device according to the techniques of this disclosure.

In general, the disclosure describes example medical devices, systems, and techniques for determining oxygenation (e.g., an amount of oxygen or an oxygen concentration) and/or flow rate of a fluid. As will be described below, examples of the disclosure may include catheters (e.g. a Foley catheter or other urinary or non-urinary catheter) and/or catheter attachments (e.g., configured to be attached to a catheter) configured to introduce one or more fluorescent probes (e.g., microbeads or other particles) into a fluid (e.g., urine) within a lumen of the catheter (e.g., the drainage lumen or lumen in fluid communication with the drainage lumen). One or more sensors positioned within or proximate to the catheter may be configured to stimulate and sense a fluorescence response from the one or more fluorescent probes in the fluid. The sensed fluorescence response of the one or more fluorescent probes may correspond to one or more parameters of the fluid, such as oxygenation or flow rate. In some examples, all or a portion of the one or more sensors may be removably coupled to the catheter body and/or catheter attachment body, e.g., such that the catheter body and/or catheter attachment may be disposed after use but all or a portion of the sensor may be reused with another catheter body and/or catheter attachment.

In some examples, the sensed parameters may be used to monitor urine output/rate of urine production of a patient and/or the amount of oxygen dissolved in the urine. Such information may be useful in monitoring the renal function of the patient, e.g., while the catheter is inserted within the patient, to detect conditions that may damage or inhibit renal function. As one example, acute kidney injury (AKI) is a complication that may occur after major surgeries, such as cardiac surgery, and other operations that are long and involve significant blood loss or fluid shifts. A primary cause of surgery-associated AKI may be hypoxia of the kidneys. When the body becomes stressed, such as during cardiac surgery, blood flow may be reduced to vital organs in a relatively consistent sequence based on the criticality of the organs. For example, the skin may be the first to realize reduced blood flow, followed by the intestines and then the kidneys, then the brain and then the heart. The skin and the intestines may withstand short hypoxic episodes and recover normal function, but the kidneys can be damaged with even brief hypoxic episodes.

This resulting renal hypoxia may cause degradation of renal function, which, after one to three days, e.g., may cause a reduced urine output and/or an accumulation of waste products in the bloodstream. This accumulation of fluid and waste products may delay the recovery of the patient leading to more extended and expensive hospital stays and sometimes requiring renal replacement therapy. Systemic vital signs like cardiac output, blood pressure, and hematocrit may be useful for detecting the accumulation of these waste products but may not always be sufficient to properly monitor the kidneys. One approach for detecting symptoms of AKI relatively early is to monitor the oxygenation status of a patient's kidneys. However, accurate monitoring may be challenging due to the inaccessibility of the kidneys, which are deep in the abdominal cavity and relatively difficult to probe using spectroscopy techniques. For example, near-Infrared spectroscopy (NIRS) may measure regional oximetry and may have some utility in infants and slender adults but may not operate with the depth of penetration and specificity required for most adults.

The present disclosure describes example medical devices configured to monitor, or aid in monitoring of, kidney function of patients, such as patients at risk of developing AKI. Medical devices described herein may include a catheter and/or a catheter attachment configured to introduce one or more fluorescent probes into urine and one or more sensors configured to stimulate and sense a fluorescence response from the one or more fluorescent probes that corresponds to parameters of the urine that are indicative of kidney function, such as oxygenation of the kidneys. In some examples, medical devices described herein may be configured to monitor the amount of oxygen dissolved in the urine coming from the bladder, as such a measurement may more accurately reflect the oxygenation of the kidneys. For example, dissolved oxygen in a patient's urine and bladder may correlate to perfusion and/or oxygenation of the kidneys, which is indicative of renal function, and may be detected relatively early and accurately compared to more variable or less responsive indicators of renal function, such as urine output or waste product accumulation. The decay of fluorescence response of the one or more fluorescent probes may indicate the amount of oxygen dissolved in the urine.

In some instances, medical devices described herein may be configured to monitor the flow rate of urine, and in some instances by using a same measurement as the measurement of oxygenation, such as by monitoring both a flow rate of urine (e.g., rate of urine production) and an amount of oxygen dissolved in the urine. For example, a fluorescence response of the one or more fluorescent probes may be related to both an amount of oxygen in the urine and a flow rate of the urine. However, an amount of urine produced by the bladder may be relatively variable over time and may involve relatively small flow rates that may be difficult to accurately measure. By using the fluorescence response of the one or more fluorescent probes to measure both the amount of oxygen dissolved in the urine and the flow rate of urine, medical devices described herein may correct for the variable flow rate of urine to more accurately measure the amount of oxygen dissolved in the urine.

For ease of description, examples of the disclosure are primarily described with regard to a catheter, such as a Foley catheter, being employed as a urinary catheter within a patient. For example, in some instances, the present disclosure is directed to a Foley catheter configured to introduce one or more fluorescent probes into a patient's urine drained via the catheter and including one or more sensors configured to facilitate detection and/or quantification of one or more physiological parameters of a patient's urine based on a fluorescence response of the one or more fluorescent probes in the urine to determine the health of the patient's kidneys (e.g., for renal monitoring). However, examples of the present disclosure are not limited to Foley-type catheters or urinary catheters.

As noted above, a Foley catheter may be a type of urinary catheter used in the examples of the present disclosure. A Foley catheter may be modified in the manner described herein to facilitate measurements of urine parameters for renal monitoring. In some examples, one or more sensors may be used in conjunction with a Foley catheter to monitor renal function to prevent acute kidney injury. In some examples, the sensor(s) may provide data indicating detection of and prevention of acute kidney injury.

FIG. 1 is a conceptual side elevation view of an example medical device 10, which includes an elongated body 12 and a hub 14. In some examples, medical device 10 may additionally include an anchoring member 18. In some examples, medical device 10 is a catheter, such as a Foley catheter. In other examples, medical device 10 may be configured to attach to catheter. While a Foley catheter and its intended use is primarily referred to herein to describe medical device 10, in other examples, medical device 10 may be used for other purposes, such as to drain wounds or for intravascular monitoring or medical procedures.

Medical device 10 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., so proximal end 12B of elongated body 12 is within the patient's urethra and bladder, distal portion 17A may remain outside of the body of the patient.

As shown in FIG. 1, elongated body 12 may be a body extending from distal end 12A to proximal end 12B and defining one or more inner lumens. In the example shown in FIGS. 1 and 2, elongated body 12 defines lumen 34 and lumen 36 (shown in FIG. 2). In some examples, lumen 34 may be a drainage lumen for draining a fluid from a target site, such as a bladder. In other examples, lumen 34 may be used for any other suitable purpose, such as a delivery lumen to deliver a substance or another medical device to a target site within a patient. Lumen 34 may extend from fluid opening 13 to fluid opening 14A. Both fluid opening 13 and fluid opening 14A may be fluidically coupled to lumen 34, so that a fluid may flow from one of fluid opening 13 or fluid opening 14A to the other of fluid opening 13 or fluid opening 14A through lumen 34. In the example where lumen 34 is a drainage lumen, fluid opening 13 and fluid opening 14A may be drainage openings. In the example shown in FIG. 1, distal end 12A of elongated body 12 is received within hub 14 and is mechanically connected to hub 14 via an adhesive, welding, or another suitable technique or combination of techniques.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal and proximal portions of elongated body 12 may each have any suitable length.

Hub 14 is positioned at a distal end of elongated body 12 and defines an opening through which the one or more inner lumens (e.g., lumen 34 shown in FIG. 2) of elongated body 12 may be accessed and, in some examples, closed. While hub 14 is shown in FIG. 1 as having two arms, 14C and 14D, (e.g., a "Y-hub"), hub 14 may have any suitable number of arms, which may depend on the number of inner lumens defined by elongated body 12. For example, each arm may be fluidically coupled to a respective inner lumen of elongated body 12. In the example of FIG. 1, hub 14 comprises a fluid opening 14A, which is fluidically coupled to lumen 34, and an inflation opening 14B, which is fluidically coupled to an inflation lumen 36 (shown in FIG. 2) of elongated body 12. In examples in which anchoring member 18 does not include an expandable balloon, rather than defining inflation lumen 36, elongated body 12 may define an inner lumen configured to receive a deployment mechanism (e.g., a pull wire or a push wire) for deploying an expandable structure anchoring member 18 and hub 14 may comprise fluid opening 14A and an opening 14B via which a clinician may access the deployment mechanism.

In examples in which medical device 10 is a Foley catheter, a fluid collection container (e.g., a urine bag) may be attached to fluid opening 14A for collecting urine draining from the patient's bladder. In other examples, a catheter attachment 50 (e.g., illustrated in FIG. 3) may be attached to fluid opening 14A, and a fluid collection container may be attached to a subsequent fluid opening 54A in catheter attachment 50 for collecting urine draining from the patient's bladder. Inflation opening 14B may be operable to connect to an inflation device to inflate anchoring member 18 positioned on proximal portion 17B of medical device 10. Anchoring member 18 may be uninflated or undeployed when not in use. Hub 14 may include connectors, such as connector 15, for connecting to other devices, such as the fluid collection container, a catheter attachment, and the inflation source. For example, connector 15 may be at least a portion of a threaded fastener and include external threads for attaching to internal threads of another device. In some examples, medical device 10 includes strain relief member 11, which may be a part of hub 14 or may be separate from hub 14.

Proximal portion 17B of medical device 10 comprises anchoring member 18 and fluid opening 13. Anchoring member 18 may include any suitable structure configured to expand from a relatively low profile state to an expanded state in which anchoring member 18 may engage with tissue of a patient (e.g., inside a bladder) to help secure and prevent movement of proximal portion 17B out of the body of the patient. For example, anchoring member 18 may include an anchor balloon or other expandable structure. When inflated or deployed, anchoring member 18 may function to anchor medical device 10 to the patient, for example, within the patient's bladder. In this manner, the portion of medical device 10 on the proximal side of anchoring member 18 may not slip out of the patient's bladder. Fluid opening 13 may be positioned on the surface of longitudinal axis of medical device 10 between anchoring member 18 and the proximal end 12B (as shown) or may be positioned at the proximal end 12B.

In accordance with examples of the disclosure, medical device 10 may include one or more sensors configured to monitor one or more parameters of a fluid within lumen 34 (FIG. 2) of elongate body 12. In the example of FIG. 1, medical device 10 includes sensor 20. Sensor 20 may be configured to sense one or more parameters of a fluid in elongate body 12, e.g., of a fluid within lumen 34 of elongate body 12, as further described below. A variety of parameters of the fluid may be sensed by sensor 20 including, but not limited to, temperature, flow rate, luminescence, fluorescence, amount of oxygen, sound, flow velocity, density, specific gravity, and the like.

Sensor 20 may be configured to detect one or more fluid parameters of a fluid flowing through lumen 34 by detecting a fluorescence or fluorescence response of one or more fluorescent probes in the fluid. As will be described below, the one or more fluorescent probes may be injected and/or supplied into the fluid and may include a fluorescent material that fluoresces and/or emits a fluorescence response based on a fluid parameter. The fluorescence response may be detectable by a sensor, e.g., sensor 20. In some examples, the one or more fluorescent probes may respond to a stimulus (e.g., emitted light) in proportion to oxygen, e.g., an amount of oxygen or an oxygen concentration within the fluid, and/or a flow rate of the fluid.

The one or more fluorescent probes may be composed of or coated and/or lined with a fluorescent and/or luminescent material. The fluorescence material may include any material that fluoresces in response to exposure to light. For example, the fluorescence material may absorb light to reach an excited state and emit light at a lower wavelength to return to a relaxed state. A variety of fluorescence materials may be used including, but not limited to, platinum octaethylporphyrin (PtOEP), phosphors such as palladium (Pd)-porphyrin, PdTPTBP/PtTPTBP (e.g., palladium(ii)/platinum(ii) tetraphenyltetrabenzoporphyrin); Ir(Cs)$_2$acac (e.g., iridium(iii) bis-(benzothiazol-2-yl)-7-(diethylamino)-coumarin-(acetylacetonate)); and/or Ru-dpp (e.g., ruthenium(ii) tris-4,7-diphenyl-1,10-phenanthroline).

In some examples, the one or more fluorescent probes may include a plurality of microbeads. The plurality of microbeads may be configured to disperse into a fluid, such as urine, within lumen 34 of medical device 10. For example, the plurality of microbeads may have dimensional (e.g., size) and/or surface properties (e.g., charge) that may be selected such that the plurality of microbeads may be suspended in the fluid, may mix into the fluid, and/or may resist agglomeration in the fluid. The microbeads may have a diameter from about 100 nm to a maximum size determined by the cross-sectional size of the lumen, e.g., about 16 French in some examples (e.g., 2.3 mm or the diameter of lumen 34). In some examples, the microbeads may have a diameter from 5 μm to 1 mm.

The plurality of microbeads may be configured to fluoresce in response to light stimuli, e.g., exposure to light, with a fluorescence lifetime proportional to the oxygen concentration of the urine. In some examples, the plurality of microbeads may include a bulk fluorescent material and/or may include a non-fluorescent core that is lined and/or coated with a fluorescent material. A variety of materials may be used for the plurality of microbeads including, but not limited to, polymer beads, glass beads, silica beads, and the like.

In accordance with examples of the disclosure, medical device 10 may be configured to introduce and/or inject one or more fluorescent probes into a fluid within lumen 34. In the example of FIG. 1, medical device 10 includes probe tank 40 in fluid communication with probe conduit 42, which is in fluid communication with lumen 34 at opening 44. In some instances, probe tank 40, probe conduit 42, and/or opening 44 may be configured to reduce or prevent a fluid from lumen 34 flowing in probe conduit 42, such as by covering opening 44 or maintaining a probe conduit 42 and probe tank 40 at a higher fluid pressure.

Probe tank 40 may contain the one or more fluorescent probes, for example, a plurality of microbeads including a fluorescent material. Probe tank 40 may be configured to deliver and/or inject the one or more fluorescent probes into the fluid. For example, probe tank 40 may passively inject microbeads into the fluid via a spring pushing a piston and forcing microbeads from probe tank 40 into probe conduit 42 and into urine flowing in lumen 34 at a controlled rate corresponding to the force the spring exerts on the piston. In other examples, probe tank 40 may actively inject one or more fluorescent probes into the fluid. For example, a motor may rotate a screw-drive at a predetermined rate pushing a piston and forcing microbeads from probe tank 40 into probe conduit 42 and into urine flowing in lumen 34, and the motor may be turned on and off or the rate changed via control circuitry. In other examples, air or fluid pressure may be used to push one or more probes from probe tank 40 into probe conduit 42, either passively controlled, actively controlled, or controlled by a user depressing a plunger on syringe. Probe tank 40 may be configured to deliver and/or inject the one or more probes via any method.

Opening 44 may be configured to receive the one or more fluorescent probes. Opening 44 may be located upstream of sensor 20. In some examples, opening 44 may be positioned relative to sensor 20 such that the one or more fluorescent probes may have sufficient time to mix prior to flowing past sensor 20. For example, opening 44 may be located a distance upstream of sensor 20 so as allow the one or more probes, e.g., a plurality of microbeads, to disperse within the fluid before flowing to the location of sensor 20. In some examples, opening 44 may be 1 mm, 1 cm, 10 cm, or any distance upstream of sensor 20.

In some examples, medical device 10 may include a check valve (not shown) configured to reduce or substantially prevent the flow of fluid to the patient's bladder and/or reduce or substantially prevent the flow of microbeads to the patient's bladder. For example, a check valve may be located at proximal end 12B, between proximal end 12B and opening 44, or at any location suitable for preventing microbeads from flowing into the patient's bladder.

Sensor 20 may be positioned on distal portion 17A of elongated body 12 of medical device 10 including portions of elongated body 12 positioned distal to distal end 12A connected to a fluid collection container (e.g., a urine bag) or the like. Sensor 20 may be positioned distal of, e.g., downstream from opening 44 by a distance equal to or greater than a length required to disperse the one or more fluorescent probes within the fluid in lumen 34. In some examples, sensor 20 is mechanically connected to elongated body 12 or another part of medical device 10 using any suitable technique, such as, but not limited to, an adhesive, welding, by being embedded in elongated body 12, via a crimping band or another suitable attachment mechanism or combination of attachment mechanisms. Sensor 20 may be removably coupled to elongated body 12. That is, sensor 20 may be coupled to elongated body 12 and used for a procedure and then sensor 20 may be removed, coupled to another elongated body and used again. In some examples, elongated body 12 includes a structure distal to a distal end of medical device 10, such as tubing extending between hub 14 and a fluid collection container, which sensor 20 may be coupled to.

In some examples, sensor 20 may be disposable and/or reusable. In some examples, sensor 20 may be disposed of, such as placed into medical waste, when elongated body 12 is through being used for a medical procedure. In some examples, all or a portion of sensor 20 may be reusable and detachable from elongated body 12 so sensor 20, or a portion thereof, may be used again on another elongated body for the same, a similar or a different procedure. For purposes of the disclosure disposable may be defined as an article intended to be used once, or until no longer useful, and then thrown away. Reusable may be defined as an item which can be used again or more than once. A reusable sensor may be configured such that sensor may be coupled to elongate body 12 so that it functions as described in the examples of the disclosure, subsequently removed from elongate body 12 and then coupled to another elongate body in a manner that allows the sensor to again function as described herein on the other elongated body.

Sensor 20 may be configured to sense or otherwise monitor a composition of a fluid (e.g., an amount or concentration of oxygen within the fluid) within elongated body 12 using a fluorescence lifetime technique. Oxygen may be sensed using a fluorescence lifetime technique. A fluorescence (or luminescence) material may be exposed to a certain wavelength or range of wavelengths (i.e. absorption spectrum) of light and absorb the light to enter an excited state. In response to enter this excited state, the fluorescence material may fluoresce by emitting light at certain wavelengths (i.e. emission spectrum) to enter a relaxed state. In certain materials, the rate at which the intensity of the fluorescence fades may be inversely proportional to the amount of oxygen in the surrounding fluid. For example, oxygen molecules may quench the fluorescence response, such that increase in an amount or concentration of oxygen may correspond to an increase in a rate of fading of the fluorescence response (i.e., a rate of fluorescence decay). As such, by measuring the rate of fluorescence decay, sensor 20 may measure an amount or concentration of oxygen in the fluid.

Sensor 20 may be configured to stimulate and measure a fluorescence response in the one or more fluorescent probes. For example, sensor 20 may include a light source configured to emit light to expose the fluorescence material of one or more fluorescent probes injected into the fluid to the emitted light. In such a configuration, the fluorescence material within the fluid may fluoresce when exposed to the light in lumen 34. Sensor 20 may also include a light detector configured to detect the fluorescence of the fluorescence material. Sensor 20 may be configured to detect oxygen in the fluid within lumen 34 based on the detected fluorescence. For example, the fluorescence material may glow or fluoresce when exposed to the light. In some materials, the rate at which the fluoresce fades is inversely proportional to the amount of oxygen it is exposed to. In such materials, the more oxygen present, the faster the fluorescence fades. By measuring the rate of fluorescence decay, sensor 20 may accurately measure the amount of oxygen in the fluid flowing within lumen 34, e.g., on a periodic or substantially continuous basis over a period of time.

In some examples, sensor 20 may be configured to sense at least one flow parameter of a fluid within lumen 34 of elongated body 12. For example, the fluorescence response from the one or more fluorescent probes may represent a flow rate of a particular component, such as oxygen, in the fluid. Due to variable amounts of urine production, this component flow rate may not be proportional to a concentration of the component in the fluid. To more accurately detect and/or determine an amount or concentration of component in the fluid, medical device 10 may be configured to detect and/or determine a flow rate of the fluid within lumen 34.

In some instances, medical device 10 may be configured to detect at least one flow parameter of the fluid by batch release of the one or more fluorescent probes. For example, probe tank 40 may inject the one or more probes into the fluid in discrete boluses. Each bolus may include an amount of the one or more probes, e.g., a predetermined number of microbeads, a predetermined mass of microbeads, a predetermined volume of microbeads and the like. In some examples, probe tank 40 may inject the one or more probes for a certain amount of time, stop the injection of the one or more probes for another amount of time, and then repeat the injection/stopping of the one or more probes in a periodic, or non-periodic predetermined manner. Sensor 20 may detect an intensity, a time duration, and rate of fluorescence decay of each bolus, and may detect a time duration between boluses, any combination of which may be used to calculate the volumetric flow rate of the fluid.

In some instances, medical device 10 may be configured to detect at least one flow parameter of the fluid by continuous release of the one or more fluorescent probes. Any suitable technique may be used to determine the at least one flow parameter of the fluid. In some examples, sensor 20 may be configured to capture a sequence of images of the fluorescing microbeads as they flow with the fluid and a determination of the at least one flow parameter may be based on the sequence of images. In other examples, sensor 20 may be configured to determine at least one flow parameter based on speckle contrast imaging. For example, probe tank 40 may be configured to continuously supply microbeads into the fluid over a period of time. Sensor 20 may be configured to detect an image of the fluorescence of the plurality of fluorescing microbeads which may approximate a dispersion of a plurality of point-like discrete light sources in a volume and may be analogous to a speckle field, such as used with speckle contrast imaging and/or decorrelation speckle imaging, e.g., when imaged with an optical band-pass filter. Sensor 20 may detect and/or capture one or more images the point-like fluorescent light sources comprising fluorescing microbeads, and processing circuitry may be configured to quantify the motion of the fluorescing microbeads to calculate a flow rate of the fluid within the lumen, as further described below.

In some examples, sensor 20 may be configured to determine at least one flow parameter based on changes in optical intensity due to motion of the microbeads in the fluid. For example, the detection area and/or volume may be configured to be substantially small such that the detected intensity of fluorescent light from the fluorescing microbeads fluctuates based on microbeads entering and leaving the detection area and/or volume. The rate of microbeads entering and leaving the optical detection area and/or volume may be determined based on the rate of fluctuations of detected intensity, and a flow rate of the fluid may be determined based on the rate of microbeads entering and leaving the optical detection area and/or volume. In some examples, microbeads may be counted per unit time (e.g., a microbead rate) based on detected fluorescent fluctuations, and a flow rate may be determined based on the microbead rate.

Sensor 20 may communicate sensor data to external device 24 via an electrical, optical, wireless or other connection. In some examples, sensor 20 may communicate sensor data to external device 24 through a connection(s) within elongated body 12 of medical device 10 from proximal portion 17B to distal portion 17A via embedded wire(s) or optical cable(s). In other examples, sensor 20 may communicate sensor data to external device 24 via a wireless communication technique.

External device 24 may be a computing device, such as a workstation, a desktop computer, a laptop computer, a smart phone, a tablet, a server or any other type of computing device configured to receive, process and/or display sensor data. Sensor 20 may communicate sensor data to the external device via a connection 26. Connection 26 may be an electrical, optical, wireless or other connection.

Many sensors require calibration information to be accurate. Sensors may provide increasingly accurate measurements with sensor-specific calibration information to compensate for variability in the sensors. For example, a fluorescence lifetime oxygen sensor may have calibration parameters related to the fluorescing material used, as well as the specifics of the light source and light detector.

Sensor 20 may use calibration information to increase an accuracy of measurements. Flow sensors and oxygen sensors may use sensor-specific calibration information to produce an accurate measurement and compensate for variability in sensor 20. For example, a fluorescent material may be temperature-dependent and therefore, to obtain a more accurate oxygen measurement, it may be helpful to know the temperature of the fluid. Sensor 20 may include additional sensors, e.g., one or more temperature sensors configured to determine a temperature of the fluid. In some examples, medical device 10 may include one or more temperature sensors at other locations along elongated body 12, e.g., spaced from sensor 20 rather than included with sensor 20. The one or more temperature sensors may be upstream or downstream from sensor 20, or near sensor 20, or included with sensor 20, and may be used as the reference for the temperature of the fluid.

Sensor 20 may have memory on sensor 20 that stores sensor calibration information, which may be used, e.g., by external device 24, to more accurately read sensor data being sent from sensor 20. Additionally, or alternatively, medical device 10 may include memory 19 and memory 19 may store sensor calibration information to calibrate sensor 20 based on the sensor calibration information stored by memory 19. Through including the sensor calibration in the sensor or memory 19 accuracy of the measurement may increase. Further, the ability to change components in a sensor or offer different ranges of sensors in the future without changing the monitoring software may provide flexibility.

Memory 19 may be located on elongated body 12 or hub 14. In some examples, all or a portion of memory 19 may be removable from elongated body 12 and may be located on or adjacent with sensor 20. Data sensed by sensor 20 may be stored on memory 19, e.g., for later retrieval by external device 24 and/or for processing of the sensor data from sensor 20. While memory 19 is shown as being separate from sensor 20, in some examples, sensor 20 may additionally or alternatively include another memory for storing data from sensor 20.

In some examples, memory 19 may include all or a portion of calibration data for sensor 20. Processing circuitry may store sensor data within memory 19 and communicate this data with external device 24. In some examples, medical device 10 may have processing circuitry on elongated body 12 or hub 14 that may control all or some operations of sensor 20. In some examples, the processing circuitry of external device 24 may control all or some operations of sensor 20. In some examples, the processing circuitry of external device 24 and processing circuitry of medical device 10 may control all or some of operations of sensor 20 together. Memory 19 may also store calibration information for sensor 20. This calibration information may assist in providing calibration information to sensor 20 and thus improve the collecting of more accurate information from sensor 20. Memory 19 may also receive information from external device 24, which memory 19 may retain onboard after disconnection from external device 24. Further, memory 19 may then share this information with another external device in the event external device 24 breaks down or in the more likely event the patient to whom medical device 10 is inserted into may be moved from surgery to an intensive care. In intensive care, memory 19 may now communicate with another external device and share information collected from surgery.

Memory 19 may store program instructions, such as software or algorithms, which may include one or more program modules, which are executable by processing circuitry (not shown in FIG. 1). When executed by the processing circuitry, such program instructions may cause the processing circuitry and external device 24 to provide the functionality ascribed to them herein. The program instructions may be embodied in software and/or firmware. Memory 19 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Elongated body 12 may be structurally configured to be relatively flexible, pushable, and relatively kink- and buckle-resistant, so it may resist buckling when a pushing force is applied to a relatively distal portion of medical device 10 to advance elongated body 12 proximally through the urethra and into the bladder. Kinking and/or buckling of elongated body 12 may hinder a clinician's efforts to push the elongated body proximally. Any suitable material may be used for elongated body 12, such as a suitable biocompatible polymer or other biocompatible material.

Figure 2:
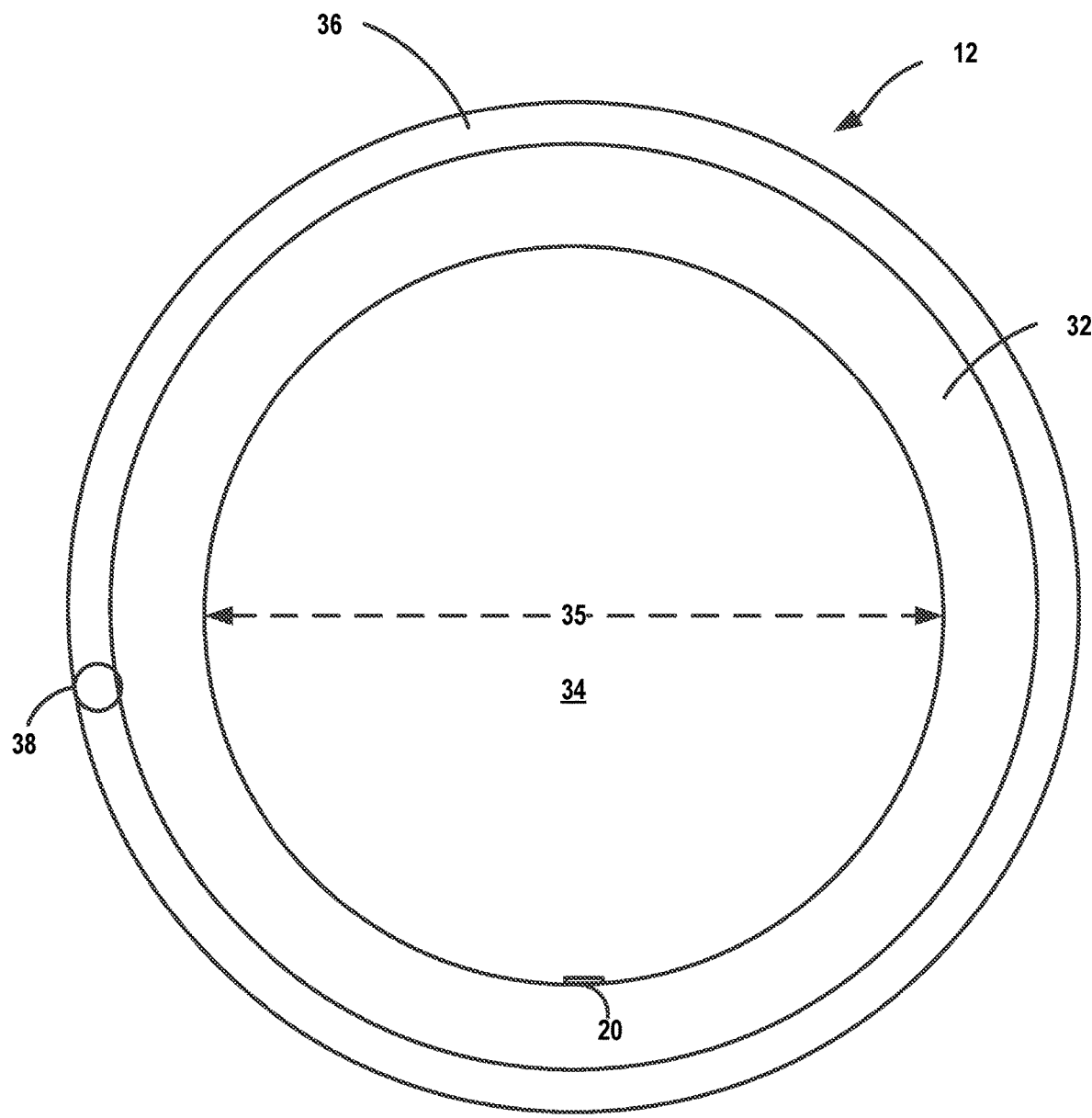
FIG. 2 is a diagram illustrating example a cross-section taken along line 1-1 of the medical device of FIG. 1 according to the techniques of this disclosure.

FIG. 2 is a diagram illustrating an example cross-section of medical device 10, where the cross-section is taken along line 1-1 in FIG. 1 in a direction orthogonal to central longitudinal axis 16. FIG. 2 depicts a cross section of elongated body 12, which defines lumen 34 and lumen 36. In some examples, lumen 34 may be referred to as a drainage lumen, such as in examples in which medical device 10 is a Foley catheter configured to drain urine from a bladder of a patient, and lumen 36 may be referred to as an inflation lumen in examples in which lumen 36 is configured to deliver an inflation fluid to anchoring member 18. Elongated body 12 may enclose connection 38.

Lumen 34 may be configured to serve as a passage for urine entering medical device 10 through fluid opening 13 to fluid opening 14A. In the example shown in FIG. 2, lumen wall 32 is relatively non-permeable to substances of interest, such as oxygen and/or carbon dioxide, and positioned between lumen 36 and lumen 34. In some examples, lumen wall 32 extends along an entire length of lumen 34, while in other examples, lumen wall 32 extends along a part of a length of lumen 34, for example, from a portion of lumen 34 intended to be in a patient's bladder during use, which may help maintain a desired level of flexibility of elongated body 12. In addition, as shown in FIG. 2, in some examples, lumen wall 32 extends around an entire outer perimeter of lumen 34 (e.g., an outer circumference in examples in which the inner perimeter is circular in cross-section).

Inflation lumen 36 may be configured to serve as a passage for a fluid, such as sterile water or saline, or a gas, such as air, from inflation opening 14B to anchoring mechanism 18. For example, an inflation device (not shown) may pump fluid or gas into inflation lumen 36 through inflation opening 14B into anchoring member 18 so anchoring member 18 is inflated to a size suitable to anchor medical device 10 to the patient's bladder. While inflation lumen 36 is shown as circular in cross section, it may be of any shape. In some examples, there may be a plurality of inflation lumens. For example, a plurality of inflation lumens may substantially surround lumen 34. In some examples, anchoring member 18 may be an expandable structure not an inflatable balloon. In such examples, inflation lumen 36 may be replaced by a deployment mechanism which may permit a clinician to expand the expandable structure. For example, inflation lumen may be replaced by a mechanical device pushed and pulled separately from the medical device 10 by a clinician to expand or retract the expandable structure.

Connection 38 may be configured to connect sensor 20 positioned at distal portion 17A to connection 26 and/or memory 19. Connection 38 may be an electrical, optical or other connection. In some examples, connection 38 may comprise a plurality of connections configured to connect different sensors to connection 26 and/or memory 19. For example, connection 38 may include one of more wired or optical connections to a temperature sensor and one or more connections to a pressure sensor. In some examples, connection 38 may include one or more power connections to provide power to sensor 20 and one or more communications connections to receive sensor data from sensor 20 and to receive calibration information from memory 19.

In examples of the disclosure, lumen 34 may have a small diameter 35 to increase the transit time of the fluid within lumen 34. In some Foley Catheters, the drainage lumen cross-sectional area may be maximized to maximize the flow rate. Adult Foley Catheters may be, e.g., 12, 14, or 16 French (e.g., with a drainage lumen diameter of about 1.3 mm to about 2.6 mm). For a given flow rate, as the cross-sectional area increases the transit time of fluid through lumen 34 decreases. Drainage lumen 34 may have a relatively small cross-sectional area, e.g., to decrease the flow rate and increase fluid transit time. Through increasing the transit time, physical characteristics of the fluid (e.g., oxygen, temperature, etc.) are preserved which increases the accuracy and utility of measurements. In some examples, diameter 35 may be about 0.75 mm to about 1.25 mm. A small inner diameter 35 of lumen 34 with an increased wall diameter (e.g., thicker walls 32) may contribute to the preservation of sensor measurements by also decreasing the gas permeability of elongated body 12. Further, the diameter of lumen 34 may be continuous over the length of elongate body 12 or it may vary. In some examples, the lumen diameter is tailored based on the location of sensor 20, e.g., to increase the accuracy of the measurement by modifying or otherwise controlling the transit time of the fluid relative to the location at which sensor 20 is sensing the fluid. For example, lumen 34 may decrease in diameter relative to the location of sensor 20 so that the transit time of the fluid decreases in the area that sensor 20 is sensing the fluid. This may be useful with a thermal dilution flow sensor such as that described herein where a decrease in diameter 35 may increase the effect of heating a flowing fluid and better detect the temperature difference. In some examples, a narrow lumen may expand the diameter at a sensor location on the elongated body of the catheter. This expansion of the diameter may increase sensor sensitivity and accuracy by increasing the time the fluid spends at the sensor location.

Figure 3:
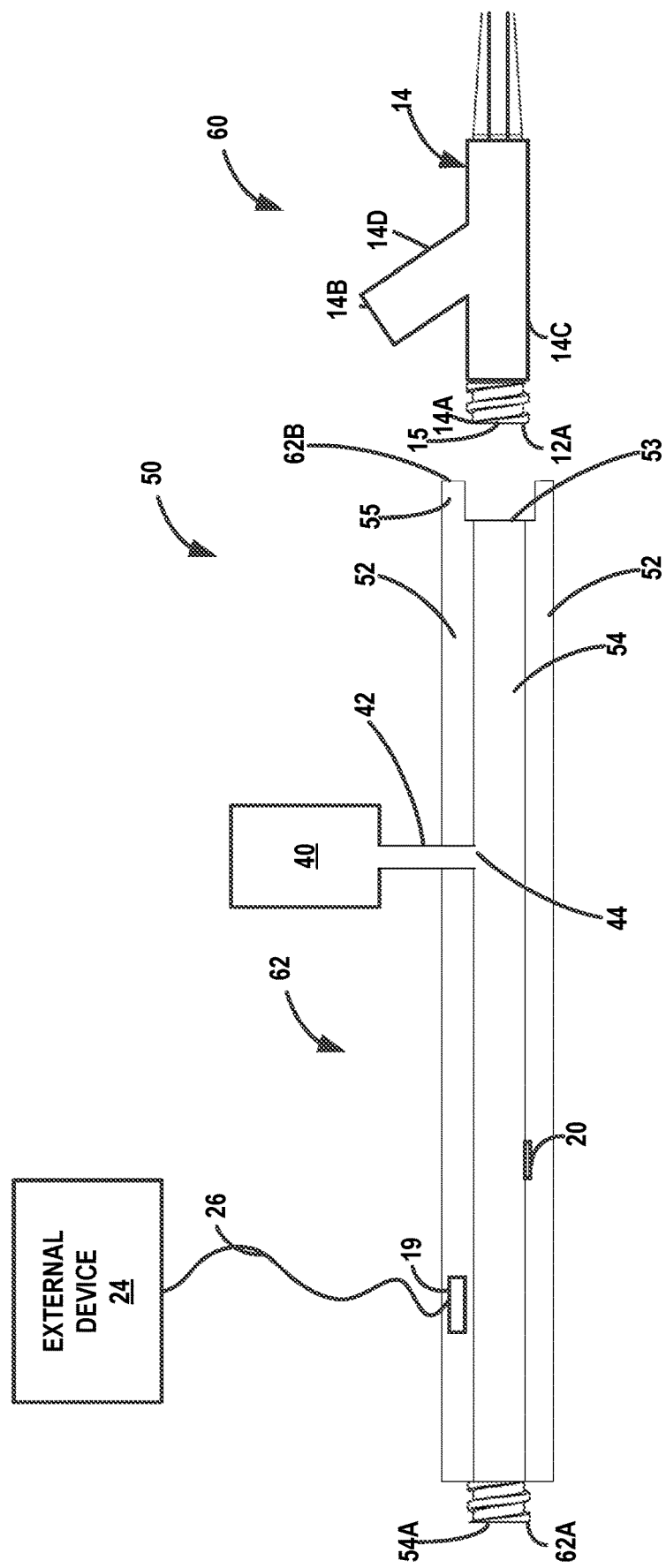
FIG. 3 is a diagram illustrating another example medical device, in accordance with one or more techniques of this disclosure.

In some instances, medical devices described herein may attach to an existing medical device for providing additional sensing functionality to the medical device. FIG. 3 is a diagram illustrating another example medical device 50, in accordance with one or more techniques of this disclosure. FIG. 3 is a conceptual side elevation view of medical device 50. In some examples, medical device 50 may be a catheter attachment configured to attach to a catheter, such as a Foley catheter. In the example of FIG. 3, medical device 50 may be configured to attach to a medical device 60. For example, connector 55 of medical device 50 may include internal threads which may receive external threads of connector 15 of medical device 60, such as described with reference to medical device 10 of FIG. 1 and reproduced in part in FIG. 3. In other examples, medical device 50 may attach to a catheter by any suitable means such that fluid from the catheter may flow into lumen 54 through fluid opening 53 of medical device 50, e.g., from fluid opening 14A at distal end 12A of medical device 60.

As shown in FIG. 3, elongated body 62 may be a body extending from distal end 62A to proximal end 62B and that defines inner lumen 54. For example, elongated body 62 defines lumen 54, which may be substantially similar to lumen 34 as illustrated in FIG. 2. In some examples, lumen 54 may be fluidically connected to lumen 34 and serve as an extension to lumen 34. Lumen 54 may extend from fluid opening 53 to fluid opening 54A. Both fluid opening 53 and fluid opening 54A may be fluidically coupled to lumen 54, so that a fluid may flow from one of fluid opening 53 or fluid opening 54A to the other of fluid opening 53 or fluid opening 54A through lumen 54. In some examples, a fluid collection container (e.g., a urine bag) may be attached to fluid opening 54A for collecting urine draining from the patient's bladder.

In some examples, elongated body 62 has a suitable length for detecting one or more fluid parameters using fluorescent probes. In some examples, elongated body 62 may have an outer diameter substantially similar to elongated body 12, but other dimensions may be used in other examples.

In accordance with examples of the disclosure, medical device 50 may include one or more sensors which may be configured to monitor one or more parameters of a fluid within lumen 54 of elongate body 62. For example, in FIG. 3, medical device 50 includes sensor 20. As described above with reference to medical device 10, sensor 20 may be configured to sense one or more parameters, such as a temperature, flow rate, light, fluorescence, amount of oxygen, sound, flow velocity, density or specific gravity of a fluid in elongate body 62, e.g., of a fluid within lumen 54 of elongate body 52.

In accordance with examples of the disclosure, medical device 50 may be configured to introduce and/or inject one or more fluorescent probes into a fluid within lumen 54, similar to medical device 10 described above. For example, medical device 50 may include probe tank 40 in fluid communication with probe conduit 42, which is in fluid communication with lumen 54 at opening 44. Opening 44 may be covered so as to prevent a fluid flowing in lumen 54 from flowing into probe arm 42, or probe tank 40 and probe arm may otherwise be configured to prevent a fluid from flowing into probe arm 42 and probe tank 40, e.g., via a higher fluid pressure.

Probe tank 40 may contain one or more fluorescent probes and may be configured to deliver and/or inject the one or more fluorescent probes into the fluid, such as described above. The one or more fluorescent probes may be a fluorescent material that may be injected and/or supplied into the fluid and that fluoresces and/or emits a fluorescence response based on a fluid parameter and the fluorescence response may be detectable by a sensor, e.g., sensor 20, such as described above with respect to FIG. 1. Opening 44 may be configured to receive the one or more fluorescent probes, e.g., via probe conduit 42, and may be positioned relative to sensor 20 such that the one or more fluorescent probes may have sufficient time to mix prior to flowing past sensor 20, such as described above with respect to FIG. 1. In some examples, medical device 50 may include a check valve (not shown) configured to reduce or substantially prevent the flow of fluid from lumen 54 to lumen 34, and/or reduce or substantially prevent the flow of microbeads to the patient's bladder. For example, a check valve may be located at fluid opening 53, between fluid opening 53 and opening 44, or at any location suitable for preventing microbeads from flowing into the patient's bladder.

Sensor 20 may be positioned along elongated body 62 of medical device 50, including portions of elongated body 62 positioned distal to distal end 62A connected to a fluid collection container (e.g., a urine bag) or the like. Sensor 20 may be positioned distal of, e.g., downstream from opening 44 by a distance equal to or greater than a length required to disperse the one or more fluorescent probes within the fluid in lumen 54. In some examples, sensor 20 is mechanically connected to elongated body 62 or another part of medical device 50 using any suitable technique, such as, but not limited to, an adhesive, welding, by being embedded in elongated body 62, via a crimping band or another suitable attachment mechanism or combination of attachment mechanisms. Sensor 20 may be removably coupled to elongated body 62. That is, sensor 20 may be coupled to elongated body 62 and used for a procedure and then sensor 20 may be removed, coupled to another elongated body and used again. In some examples, elongated body 62 includes a structure distal to a distal end of medical device 50, such as tubing extending distal end 62A and a fluid collection container, which sensor 20 may be coupled to.

In some examples, sensor 20 may be disposable and/or reusable, such as described with respect to FIG. 1 above. Sensor 20 may be configured to sense or otherwise monitor a composition of a fluid (e.g., an amount or concentration of oxygen within the fluid) within elongated body 62 using a fluorescence lifetime technique, such as described above with respect to FIG. 1 and with reference to elongated body 12. Additionally, sensor 20 may be configured to sense at least one flow parameter of a fluid within lumen 54 of elongated body 62, such as described above with respect to FIG. 1 and with reference to lumen 34 and elongated body 12. For example, the fluorescence response from the one or more probes may represent a flow rate of a particular component, such as oxygen, in the fluid. In some instances, medical device 50 may be configured to detect at least one flow parameter of the fluid by batch release and/or continuous release of the one or more fluorescent probes, such as described above with respect to FIG. 1 and with reference to medical device 10.

As described above, sensor 20 may communicate sensor data to external device 24 via an electrical, optical, wireless or other connection. In some examples, sensor 20 may communicate sensor data to external device 24 through a connection(s) within elongated body 62 of medical device 50 via embedded wire(s) or optical cable(s). In other examples, sensor 20 may communicate sensor data to external device 24 via a wireless communication technique. In some examples, and similar to as described above, sensor 20 may require calibration, and may have memory that stores sensor calibration information. Additionally, or alternatively, medical device 50 may include memory 19 and memory 19 may store sensor calibration information to calibrate sensor 20 based on the sensor calibration information stored by memory 19. Through including the sensor calibration in the sensor or memory 19 accuracy of the measurement may increase. Further, the ability to change components in a sensor or offer different ranges of sensors in the future without changing the monitoring software may provide flexibility.

Memory 19 may be located on elongated body 62. In some examples, all or a portion of memory 19 may be removable from elongated body 62 and may be located on or adjacent with sensor 20. Data sensed by sensor 20 may be stored on memory 19, e.g., for later retrieval by external device 24 and/or for processing of the sensor data from sensor 20. While memory 19 is shown as being separate from sensor 20, in some examples, sensor 20 may additionally or alternatively include another memory for storing data from sensor 20.

In some examples, memory 19 may include all or a portion of calibration data for sensor 20. Processing circuitry may store sensor data within memory 19 and communicate this data with external device 24. In some examples, medical device 50 may have processing circuitry on elongated body 62 that may control all or some operations of sensor 20. In some examples, the processing circuitry of external device 24 may control all or some operations of sensor 20. In some examples, the processing circuitry of external device 24 and processing circuitry of medical device 50 may control all or some of operations of sensor 20 together. Memory 19 may also store calibration information for sensor 20. This calibration information may assist in providing calibration information to sensor 20 and thus improve the collecting of more accurate information from sensor 20. Memory 19 may also receive information from external device 24, which memory 19 may retain onboard after disconnection from external device 24. Further, memory 19 may then share this information with another external device in the event external device 24 breaks down or in the more likely event the patient to whom medical device 50 is attached may be moved from surgery to an intensive care. In intensive care, memory 19 may now communicate with another external device and share information collected from surgery.

As described above, memory 19 may store program instructions, such as software or algorithms, which may include one or more program modules, which are executable by processing circuitry (not shown in FIG. 1). When executed by the processing circuitry, such program instructions may cause the processing circuitry and external device 24 to provide the functionality ascribed to them herein. The program instructions may be embodied in software and/or firmware. Memory 19 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Elongated body 62 may be structurally configured to be relatively flexible, pushable, and relatively kink- and buckle-resistant, so it may resist buckling when a pushing force is applied to a relatively distal portion of medical device 50. Any suitable material may be used for elongated body 62, such as a suitable biocompatible polymer or other biocompatible material.

Figure 4:
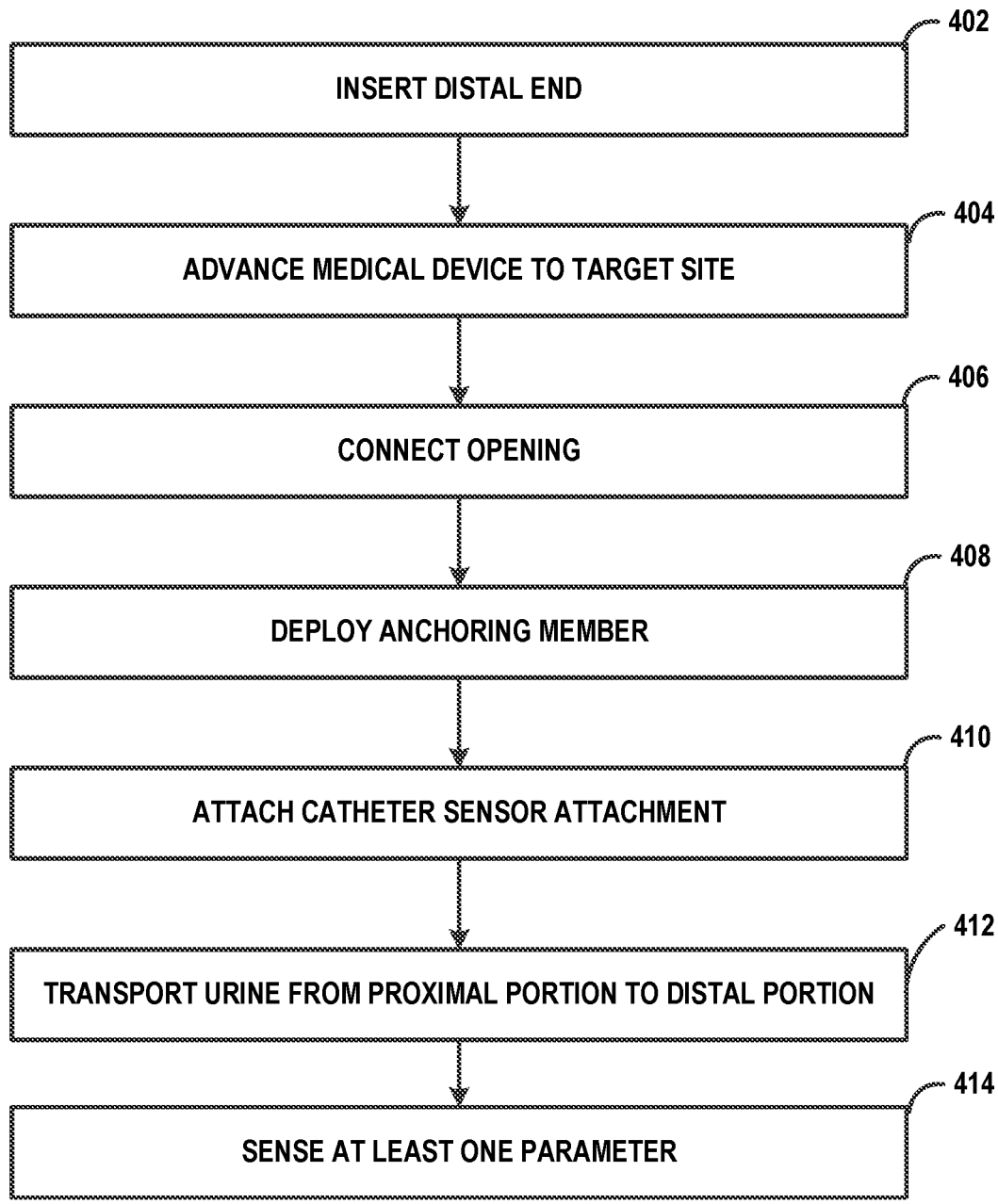
FIG. 4 is a flowchart illustrating an example method of operating a medical device according to the techniques of this disclosure.

Medical devices described herein, such as medical device 10 and/or medical device 50, may be used by a clinician to sense one or more parameters of a fluid in a patient. FIG. 4 is a flowchart illustrating an example operation of medical device 10 and/or medical device 50. A clinician may insert proximal end 12B of medical device 10 into a patient's urethra (402). The clinician may advance medical device 10 through the patient to a target site (404), e.g., until uninflated or undeployed anchoring member 18 is within the patient's bladder (404). The clinician may connect inflation opening 14B to an inflation device and may connect fluid opening 14A to a fluid collection container and/or to external sensors (406). The clinician may then deploy anchoring member 18 to help secure medical device 10 relative to the target site (408). For example, the clinician may inflate anchoring member 18, for example, using an inflation device and inflation fluid, such as sterile water, saline, or a gas. In examples in which anchoring member 18 is an expandable structure, the clinician may deploy anchoring member 18 by pushing a structure radially outwards or pulling back on a structure to cause the expandable structure to expand radially outwards.

Optionally, a clinician may attach medical device 50 to a catheter, e.g., a Foley catheter used rather than medical device 10 (410). For example, the clinician may screw medical device 50 onto a distal end of a Foley catheter, or attach medical device to the catheter by any suitable means such that lumen 54 is in fluid communication with the lumen of the catheter configured to drain urine from the patient. In some example, attachment of medical device 50 may be done prior to deploying anchoring member, connecting inflation opening, or inserting and advancing the catheter to a target site.

Lumen 34 of medical device 10 may transport urine from the proximal portion 17B of medical device 10 to the distal portion 17A of medical device 10 (412). Sensor 20 may sense at least one parameter, such as temperature and/or oxygen, from urine being transported through lumen 34 (414). For example, sensor 20 may sense a parameter such as urine flow (e.g., fluid velocity or volume), and/or amount of dissolved oxygen in the urine. In some examples, sensor 20 may sense at least one parameter between medical device 10 and a fluid collection container, e.g., at the distal end of elongate body 12.

Additionally or alternatively, lumen 54 of medical device 50 may transport urine from the proximal end 62B of medical device 50 to the distal 62A of medical device 50 (412). Sensor 20 may sense at least one parameter, such as temperature and/or oxygen, from urine being transported through lumen 54 (414). For example, sensor 20 may sense a parameter such as urine flow (e.g., fluid velocity or volume), and/or amount of dissolved oxygen in the urine, such as will be described further in FIG. 7. In some examples, sensor 20 may sense at least one parameter between medical device 50 and a fluid collection container, e.g., at the distal end of elongate body 62.

While the example of FIG. 4, sets forth a number of steps, these steps may be performed in a different order or concurrently. For example, the clinician may connect the inflation opening 14B to an inflation device and/or may connect fluid opening 14A to a fluid collection container and/or to sensor 20 prior to inserting the proximal end 12B of medical device 10 into the patient's urethra and lumen 34 may transport urine concurrently with sensor 20 sensing any parameters.

Figure 5:
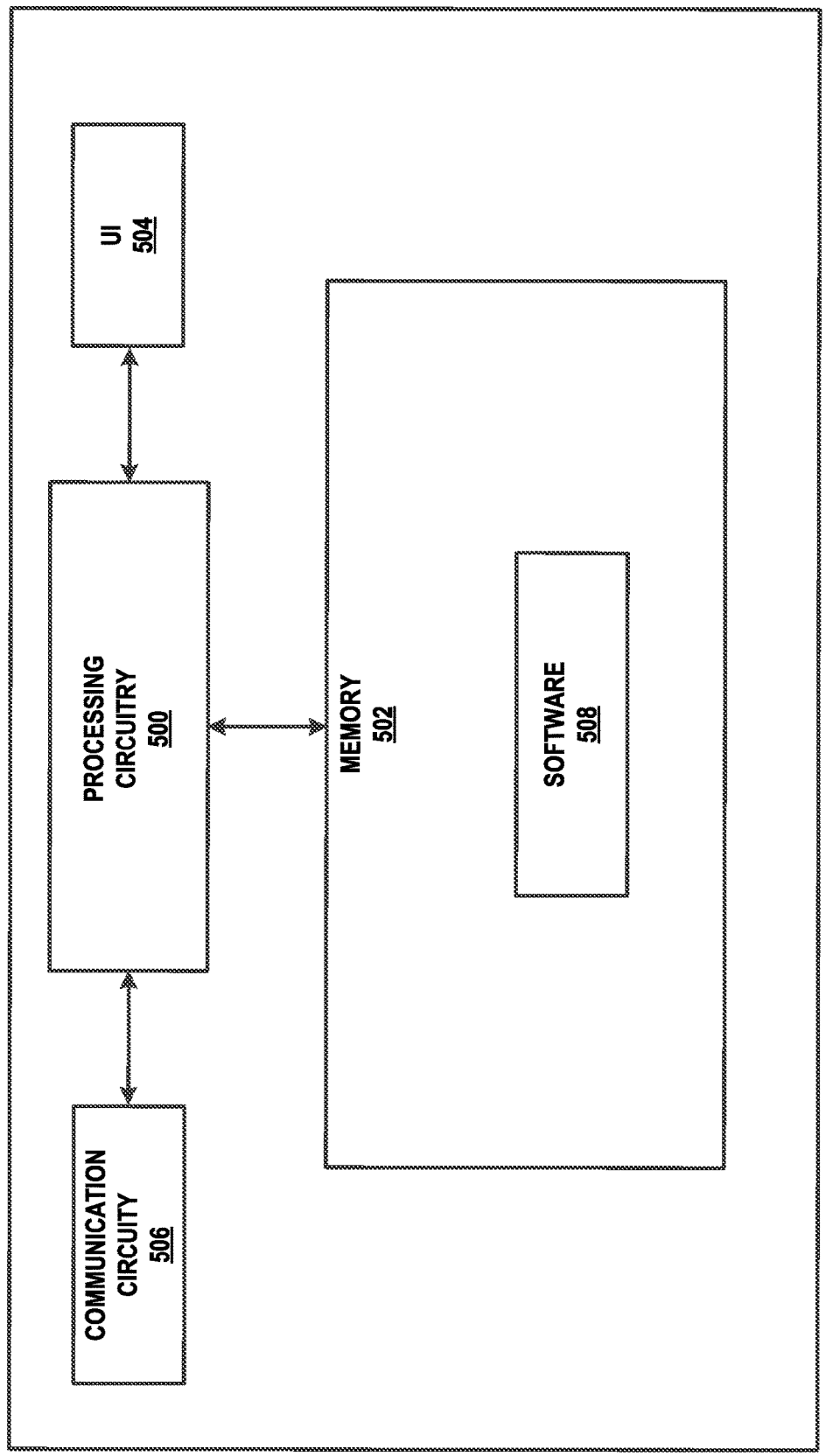
FIG. 5 is a block diagram of an example external device used with a medical device according to the techniques of this disclosure.

Medical devices described herein, such as medical device 10 and/or medical device 50, may communicate with one or more external devices, such as by receiving control signals and/or sending measurement signals. FIG. 5 is a functional block diagram illustrating an example of an external device 24 configured to communicate with sensor 20, receive information from sensor 20 and store and retrieve information from memory 19. In the example of FIG. 5, external device 24 includes processing circuitry 500, memory 502, user interface (UI) 504, and communication circuitry 506. External device 24 may be a dedicated hardware device with dedicated software for reading sensor data. Alternatively, external device 24 may be an off-the-shelf computing device, e.g., a desktop computer, a laptop computer, a tablet, or a smartphone running a mobile application enabling external device 24 to read sensor data from sensor 20 and memory 19.

In some examples, a user of external device 24 may be clinician, physician, intensivist, or heath care giver. In some examples, a user uses external device 24 to monitor a patient's kidney function, e.g., based on information sensed by sensor 20 or otherwise derived from information sensed by sensor 20 in the manner described herein. In some examples, the user may interact with external device 24 via UI 504, which may include a display to present a graphical user interface to the user, and a keypad or another mechanism (such as a touch sensitive screen) for receiving input from the user. External device 24 may communicate with sensor 20 and/or memory 19 using wired, wireless or optical methods through communication circuitry 506.

Processing circuitry 500 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 500 may include multiple components, such as any combination of one or more microprocessors, one or more DSPs, one or more ASICs, or one or more FPGAs, as well as other discrete or integrated logic circuitry, and/or analog circuitry.

Memory 502 may store program instructions, such as software 508, which may include one or more program modules, which are executable by processing circuitry 500. When executed by processing circuitry 500, such program instructions may cause processing circuitry 500 and external device 24 to provide the functionality ascribed to them herein. The program instructions may be embodied in software and/or firmware. Memory 502 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

FIGS. 6-9 illustrate various arrangements of fluorescence sensors and techniques for operating the fluorescence sensors. The fluorescence sensors of FIGS. 6 and 8 may interface with external device 24 of FIG. 5, and the techniques of FIGS. 7 and 9 may be at least partially performed by external device 24 of FIG. 5.

Figure 6:
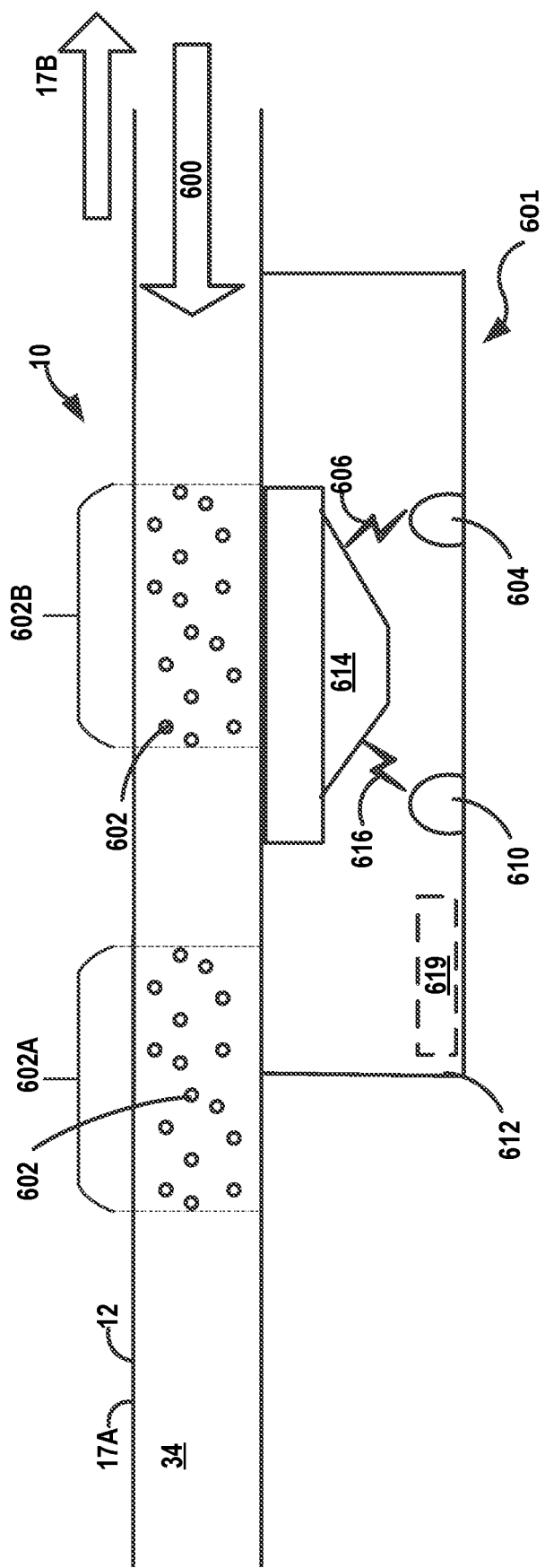
FIG. 6 is a diagram illustrating an example sensor used with a medical device according to the techniques of this disclosure.

FIG. 6 is a diagram illustrating an example fluorescence sensor 601 used with a medical device 10 and/or a medical device 50, according to the techniques of this disclosure. Fluorescence sensor 601 may be an example of sensor 20 of medical device 10 (FIG. 1) and/or medical device 50 (FIG. 3), and fluorescence sensor 601 may be used in place of sensor 20, used in combination with sensor 20 and other sensors such as temperature sensors, or in addition to sensor 20 and other sensors such as temperature sensors. In the example shown, fluid 600 is flowing from proximal portion 17B to distal portion 17A of medical device 10, as indicated by the directional arrow. Additionally or alternatively, fluid 600 may flow from proximal end 62B to distal end 62A of medical device 50.

Fluorescence sensor 601 may be configured to determine an oxygen level within fluid 600 utilizing, e.g., a fluorescence lifetime technique (FLT). Fluorescence sensor 601 includes sensor body 612 housing a light source 604, a light detector 610, and an optional lens 614. Sensory body 612 may support light source 604, light detector 610 and optional lens 614. Fluorescence sensor 601 may determine a parameter based on the sensed fluorescence. Once the determination is made, a processor (e.g., processor 500 of FIG. 5) may control a user interface (e.g., user interface 504 on external device 24) to present an indication of the determined value. For example, processor 500 may control user interface 504 of external device 24 to present an indication of oxygen saturation of fluid 600 determined with fluorescence sensor 601.

In some examples, fluorescent probes 602 may be injected, released, introduced, etc., into fluid 600 upstream of fluorescence sensor 601 and may flow with fluid 600. In the example shown, fluorescent probes 602 may be released into fluid 600 upstream of fluorescence sensor 601 as a bolus, e.g., first fluorescent probe bolus 602A and second fluorescent probe bolus 602B. In some examples, more or fewer fluorescent probe boluses may be released into fluid 600, e.g., to determine at least one fluid parameter via measurements by fluorescence sensor 601. Fluorescent probe boluses 602A and 602B may comprise a discrete amount and/or number of fluorescent probes released into fluid 600 in a predetermined amount of time. In some examples, fluorescent probes 602 of fluorescent probe boluses 602A and 602B may be configured to disperse within lumen 34 (or lumen 54) in both a longitudinal direction along lumen 34 and/or lumen 54 and the radial direction of lumen 34 and/or 54. In some examples, opening 44 (FIGS. 1 and 3) may be configured, individually or in combination with fluorescent probes 602, to release fluorescent probe boluses 602A and 602B such that the fluorescent probes of each bolus disperse by a predetermined amount by the time they flow to the region and/or location along the length of lumen 34 and/or 54 of fluorescence sensor 601. In some examples, fluorescent probes 602 may be fluorescent microbeads, e.g., polymer microbeads including a fluorescent material configured to be exposed by excitation light external to the polymer microbead. In other words, fluorescent probes 602 may comprise microbeads including a coating a fluorescent material on an outer surface, or fluorescent probes 602 may include a fluorescent material within the microbead and/or as part of the polymer. In some examples, fluorescent probes 602 may be microbeads made of other materials, such as glass, and include a coating of fluorescent material on an outer surface and/or include a fluorescent material within the microbead.

In one example, fluorescence sensor 601 is configured to sense oxygen in fluid 600 (e.g., oxygen concentration) using a FLT and based on a fluorescence response from a fluorescent material, such as fluorescent probes 602. In this technique, fluorescence material 602 is exposed to light 606 (which may be a specific wavelength or range of wavelengths) emitted from light source 604, e.g., excitation light 606. Fluorescence material 602 (referred to as a fluorescence lifetime material or an optrode), glows (fluoresces 608) when exposed to light 606. In specific materials used for fluorescent probes 602, the rate at which the glow fades is inversely proportional to the amount of oxygen the fluorescent material exposed to. In these fluorescent materials, the more oxygen (i.e., higher concentration of oxygen) that is present the faster the glow fades. By measuring the rate of glow and/or fluorescence response decay in calibrated optrodes with light detector 610, fluorescence sensor 601 may measure the amount of oxygen in fluid 600, e.g., accurately and/or substantially continuously.

In some examples, fluorescence sensor 600 may include one or more features that reduce cost and/or power consumption of fluorescence sensor 600. In some examples, fluorescence sensor 600 may be removable and configured for multiple uses. For example, when used in a Foley catheter or other catheter fluorescent probes 602 may be relatively small, e.g., to fit within lumen 34 and/or lumen 54 without substantially obstructing the flow for fluid 600 and/or to sufficiently disperse and remain suspended in fluid 600. As a result of this relatively small size, the fluorescent light 616 of the fluorescent probes 602 may have a low intensity such that, to detect fluorescent light 616, light detector 610 (referred to in some examples as a photodiode) may be relatively high-performance (e.g., sensitive), which may be expensive and large. To overcome these limitations, in some examples, fluorescent probes 602 may be disposable and within the drainage lumen 34 of the Foley catheter and/or lumen 54 of a catheter attachment, but the relatively expensive light source 604 and light detector 610 may be reusable and detachably coupled to elongated body 12 and/or 62. As illustrated in FIG. 6, in some examples, lens 614 may be a part of the disposable portion of fluorescence sensor 601. Alternatively, lens 614 may be on the re-usable portion of fluorescence sensor 601 (e.g., in addition to light source 604 and/or light detector 610).

As described herein, fluorescence sensor 601 may be an optical sensor device that optically measures a specific substance (e.g., oxygen in fluid 600) with the aid of a fluorescent probes 602 (which may be referred to as an optode or optrode). For FIT, e.g., fluorescence sensor 601 may utilize luminescence (e.g., fluorescence and phosphorescence) or chemiluminescence to measure the oxygen within fluid 600 within lumen 34 and/or lumen 54. However, other methods of optical measurement may be used. In some examples, optical sensing techniques such as reflection, absorption, evanescent wave, surface plasmon resonance, may be used.

The fluorescent material of fluorescent probes 602 may be any suitable material configured to fluoresce in response to being exposed to light 616 from light source 604 in the manner described herein, such as described with respect to the one or more fluorescent probes of FIG. 1. When exposed to excitation light 606, the fluorescence material releases fluorescent light 616. Fluorescent light 616 of the fluorescence material may be quenched, or caused to dissipate, by specific analytes (e.g., oxygen) in fluid 600. The fluorescent light 616 to oxygen ratio within fluid 600 may not be linear. Fluorescence sensor 601 may have a greater sensitivity at low oxygen concentration, (e.g., when the fluorescent light 616 is the greatest) then at high oxygen concentration (e.g., when the fluorescent light 616 is the lowest). In some examples, fluorescence sensor 601 may operate in a region of 0-100% oxygen saturation in fluids containing mostly water, such as urine, with a calibration for the type of material reacting with fluorescence material 602.

Light source 604 may be configured to emit excitation light 606. Light source 604 may be any suitable light device or devices configured to emit light 606 in the manner described herein. In some examples, light source 604 includes an LED (light emitting diode), amplified natural lighting, HID (high-intensity discharge) and/or fluorescent and incandescent source capable of emitting light 606, e.g., at an excitation wavelength. Light source 604 emits a wavelength or range of wavelengths of light configured to excite (i.e. raise an energy state of) the fluorescent material of fluorescent probes 602. The wavelength of light may be different for differing fluorescence materials (e.g., different fluorescence material chemistries have different excitation frequencies). Light source 604 may be powered by an onboard power source on fluorescence sensor 601 or maybe powered by external device 24 providing power through connection 38 (FIG. 2). In some examples, light source 604 may emit a specific wavelength of light, that causes the fluorescent material to enter an excited state.

Light detector 610 may be any type of light detector configured to detect fluorescent light 616 from fluorescent probes 602, e.g., to detect the decay of fluorescent light 616 from fluorescent probes 602 over a period of time. In some examples, light detector 610 may be a photodiode (e.g., PN photodiodes, PIN photodiodes, avalanche photodiodes (particularly well suited for fluorescence sensor due to their high sensitivity), and Schottky photodiodes), photoconductor (e.g., photoresistor), photovoltaic device (e.g., photocell), phototransistor, and/or photodiode, Light detector 610 may detect light excitation between 300 nm and 800 nm. Light detector 610 may detect the light excitation of fluorescent light 616. In some examples, processing circuitry 500 may process the light excitation data of light detector 610 to detect the time the fluorescent material spends in the excited state or otherwise detect the rate of decay of fluorescent light 616.

Lens 614 may be configured to focus light 606 emitted from light source 604 to fluorescence material 602 and/or focus fluorescence 608 to light detector 610 (as represented by light 616), In some examples, lens 614 may be optical glass, crystals, plastics, mirrors or other material that focuses light in the manner described herein. Lens 614 may focus fluorescent light 616 on light detector 610 to increase its intensity and reduce the performance requirement of light detector 610. Lens 614 may also focus light 606 from light source 604 onto fluorescent probes 602. Lens 614 may be configured to be disposable or re-usable as part of fluorescence sensor 601. In some examples, lens 614 may also have filters to optimize the delivery of excitation light 606 or sensing of fluorescent light 616. With filters, light source 604 and light detector 610 may be less precise and thus less expensive alternatives for light source 604 and light detector 610 may be used. By filtering excitation light 606 being emitted to fluorescent probes 602 and filtering fluorescence light 616 being detected by light detector 610, both light source 604 and light detector 610 may not be high performing devices and thus may be less expensive.

Sensor body 612 may be configured to house, support or otherwise couple together one or more of light source 604, light detector 610, or lens 614, e.g., in a desired arrangement. In some examples, sensor body 612 may be configured to be removably coupled to elongated body 12, e.g., to allow for a portion of fluorescence sensor 601 to be reusable with other catheters and/or catheter attachments In some examples, sensor body 612 may include a material that is used imprinted circuit board design (e.g., FR-2 (phenolic cotton paper), FR-3 (cotton paper and epoxy), FR-4 (woven glass and epoxy), FR-5 (woven glass and epoxy), FR-6 (matte glass and polyester), G-10 (woven glass and epoxy), CEM-1 (cotton paper and epoxy), CEM-2 (cotton paper and epoxy)). In another example, sensor body 612 may have a flexible design so it may contour to the cylindrical shape of elongated body 12 and/or elongated body 62, thus allowing lens 614, light source 604 and light detector 610 to be as close to elongated body 12 as possible to ensure reliable light transfer and sensor measurements. Flexible PCB materials include PI (polyimide) film and PET (polyester) film apart from which polymer film is also available like PEN (polyethylene naphthalate), PTFE and Aramid etc.

Fluorescence sensor 601, in conjunction with fluorescent probes 602, may be configured to measure one or more parameters of fluid 600 by measuring a fluorescence lifetime (FLT) of a fluorescence response from fluorescent probes 602. FLT may be the time the fluorescence material of fluorescent probes 602 spends in the excited state ($T_{es}$). In some examples, the FLT may vary from picoseconds to hundreds of nanoseconds depending on the fluorescent material. FLT may not be substantially affected by fluorescence concentration, absorption by fluid 600, thickness of fluid 600, method of measurement, fluorescence intensity, photo-bleaching and/or excitation intensity. However, FLT may be affected by external factors, such as temperature (discussed below, which may be calibrated for), polarity, and the presence of fluorescence quenchers (e.g., oxygen).

For fluorescence sensor 601 to measure a fluid parameter based on FLT, fluorescent probes 602 may be located within lumen 34 and/or lumen 54 with fluid 600 on an opposite side of lumen wall 32 and/or 52 from lens 614, light source 604 and light detector 610. When powered on, by processing circuitry 500 or a separate power source onboard (not shown) light source 604 may emit light 606, e.g., at a specific wavelength to expose fluorescent probes 602 to emitted light 606. Light source 604 may emit light 606 through elongated body 12 and/or 62. In some examples, lumen wall 32 and/or 52 may be transparent to emitted light 606 and fluorescent light 616 or otherwise configured to allow light 606 and fluorescent light 616 to be transmitted through lumen wall 32 and/or 52.

Fluorescent probes 602 within fluid 600, as discussed above, may be configured to fluoresce when exposed to light 606 in lumen 34 and/or 54. Light detector 610 may detect fluorescent light 616 of fluorescent probes 602. Processing circuitry 520 may then determine the amount of oxygen within fluid 600 by recording the time for fluorescent light 616 ($T_f$) to quench (or dissipate) or otherwise decay. Processing circuitry 500 may then determine the time to dissipate ($T_f$) with ($T_{es}$) and based upon this difference, determine how much oxygen is present within fluid 600. Further, processing circuitry such as processing circuitry 500 may calibrate for the temperature of fluid 600, which may have an effect on how quickly fluorescent light 616 dissipates.

In another example, fluorescent probes 602 may be excited with light pulses (e.g., light initiated in a sine wave pulse). Processing circuitry 500 may then determine a frequency shift of the fluorescence material response that measures the fluorescence decay time continuously. In another example, when fluorescent probes 602 are excited, the fluorescence saturation time may be measured and determined by processing circuitry 500, where the saturation time is proportional to oxygen content.

In some examples, light source 604 and light detector 610 are releasably coupled to elongated body 12 and/or 62, e.g., either separate from each other or together via the detachment of sensor body 612 from elongated body 12 and/or 62. In other examples, each of light source 604 and light detector 610 may be part of or integral with elongated body 12 and/or 62 or may be separate and coupled to elongated body 12 and/or 62 for use during a procedure. In some examples, sensor body 612 may be releasably coupled to elongated body 12 and/or 62 where sensor body 612 may support light source 604 and light detector 610. In some examples, sensor body 612 may be part of or integral with elongated body 12 and/or 62. In some examples, lens 614 may be added for improved performance of light source 604 and light detector 610 and may be placed on elongated body 12 and/or 62 in between fluorescent probes 602 and light source 604. Lens 614 may be used to focus light 606 to fluorescent probes 602 in lumen 34 and/or 54. Lens 614 may focus fluorescent light 616 from fluorescent probes 602 to light detector 610. In some examples, lens 614 may be disposed of along with elongated body 12 and/or 62 and fluorescent probes 602 when the patient no longer needs medical device 10 and/or a catheter.

Processing circuitry 500 may use time for fluorescent light 616 ($T_f$) to determine an amount of oxygen within fluid 600 within lumen 34 and/or 54. As discussed, fluorescent light 616 has a fluorescence excitation time limit ($T_{es}$) that represents a maximum time at which fluorescent probes 602 may fluoresce. Various factors, such as an amount or concentration of oxygen in fluid 600 may shorten this excitation time. For example, when oxygen molecules are present in fluid 600 and collide with fluorescent probes 602, the oxygen molecules may quench the fluorescent light 616, such as by forming ground complexes with the fluorescence probes 602 or absorbing energy from fluorescent probes 602 that may otherwise be emitted as fluorescent light 616, if fluid 600 has no oxygen present, then fluorescence time ($T_f$) may be close to or equal to the excitation state time ($T_{es}$). On the other hand, if fluid 600 has a 100% oxygen saturation, then fluorescence time ($T_f$) should be zero or substantially zero. As stated above, the relationship between fluorescence time ($T_f$) and oxygen concentration may be non-linear.

Processing circuitry 500 may determine an amount and/or concentration of oxygen based on the determined fluorescence time of fluorescent probes 602 detected by fluorescence sensor 601. In some examples, processing circuitry 500 may use an algorithm to determine the amount of oxygen within fluid 600. In another example, processing circuitry 500 may utilize a lookup table stored on memory 502, memory 619, and/or memory 19, where an oxygen content of fluid 600 is dependent on fluorescence time ($T_f$) and the temperature of fluid 600 (e.g., discussed above, temperature also affect fluorescence time).

As discussed above, the accuracy of fluorescence sensor 601 may be temperature dependent as temperature affects the fluorescence time ($T_f$). Thus, to provide accurate sensor readings, fluorescence sensor 601 may be calibrated, e.g., in real time, to obtain an accurate oxygen measurement. To obtain this measurement the temperature of fluid 600 may used. Therefore, the more accurately the temperature of fluid 600 is known, the more accurate a reading of oxygen can be obtained from fluorescence sensor 601. Processing circuitry 500 may use the temperature data collected from temperature sensors, an estimated temperature based on a patient's body temperature, another sensor coupled to external device 24 or a temperature inputted by a user at user interface 504. Processing circuitry 500 may use the temperature to input into, e.g., an algorithm or a look up table to calibrate the oxygen calculation based on temperature of fluid 600 in combination with the rate of fluorescence decay detected by light detector 610.

Fluorescence sensor 601 may be configured to determine a flow rate of fluid 600 within lumen 34 and/or 54. For example, medical device 10 and/or 50 may be configured to determine a flow rate of fluid 600 based on a batch release of fluorescent probes 602, e.g., as one or more fluorescent probe boluses. In some examples, probe tank 40 may inject the one or more probes into fluid 600 in discrete boluses. For example, fluorescent probe boluses 602A and 602B may include an amount of the one or more probes, e.g., a predetermined number of microbeads, a predetermined mass of microbeads, a predetermined volume of microbeads and the like. The amount of the one or more probes of each fluorescent probe bolus 602A and 602B and the time between each fluorescent probe bolus 602A and 602B may be predetermined. Fluorescence sensor 601 may illuminate each fluorescent probe bolus 602A and 602B with excitation light 606, detect fluorescent light 616 from each of fluorescent probe bolus 602A and 602B after excitation, and determine a flow rate based on a time duration of the detected fluorescence of one or both of fluorescent probe bolus 602A and 602B and/or a time between detecting the fluorescence of each of fluorescent probe bolus 602A and 602B.

In some examples, determining the flow rate of fluid 600 may assist in a better understanding of the dissolved oxygen measurement of fluorescence sensor 601. In an example, a low volumetric flow rate may mean the dissolved oxygen measurement of fluorescence sensor 601 may not be as accurate to renal oxygenation due to the effects of the ureter, bladder, and slow transit time through lumen 34 and/or 54. Thus, an alert may be sent to user interface 504, providing an indication the sensed oxygen may be inaccurate due to low volumetric flow. In some examples, fluorescence sensor 601 may be configured to concurrently determine the flow rate of fluid 600 and an oxygen level with fluid 600 based on the fluorescence of fluorescent probe boluses 602A and 602B. For example, fluorescence sensor 601 may be configured to determine an oxygen level based on FLT as described above for each of one or more fluorescent probe boluses, and a flow rate based on the timing and duration (e.g., volume) of two or more fluorescent probe boluses, e.g., fluorescent probe bolus 602A and 602B. In some examples, fluorescence sensor 601 may be configured to continuously measure oxygen level via FLT and correct the oxygen level determination based on flow rate measurements and subsequent oxygen level measurements of subsequent fluorescent probe boluses.

Figure 7:
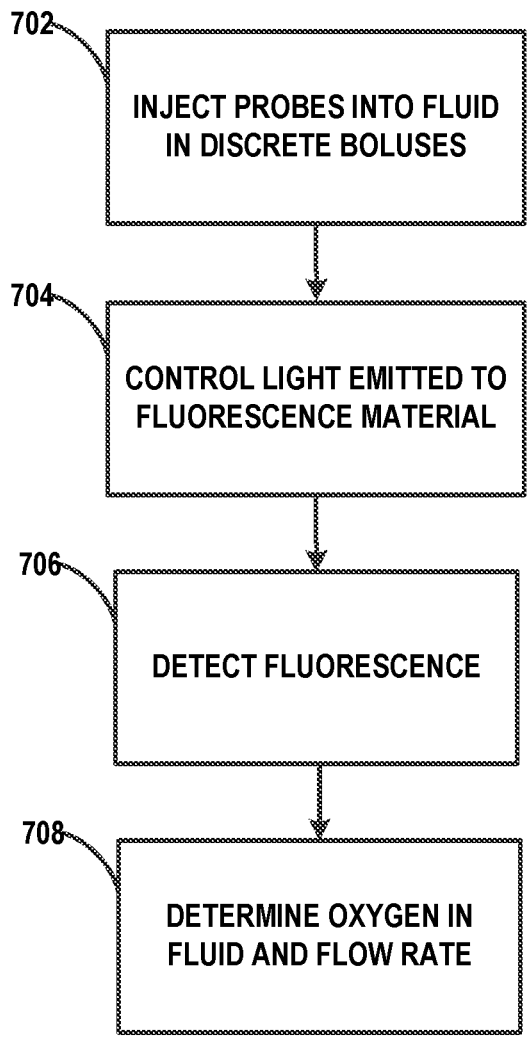
FIG. 7 is a flow diagram illustrating an example technique for monitoring or otherwise sensing oxygen and a flow rate of a fluid within a lumen, according to the techniques of this disclosure.

FIG. 7 is a flow diagram illustrating an example technique for monitoring or otherwise sensing an amount and/or concentration of oxygen in a fluid and a flow rate of a fluid within a lumen, according to techniques of this disclosure. FIG. 7 will be described with respect to FIG. 6.

A plurality of fluorescent probes 602 may be injected into a fluid flowing in a lumen of elongated body 12 and/or 62 (702). For example, a probe tank, such as probe tank 40 of FIG. 1, may be fluidically connected to lumen 34 and/or 54 via a probe conduit and an opening into lumen 34 and/or 54. Processing circuitry 500 may cause an amount, volume, mass, and/or number of fluorescent probes 602 may be released from probe tank 40 into lumen 34 and/or 54 one or more times as one or more boluses, e.g., fluorescent probe boluses 602A and 602B. The amount of the one or more probes of each fluorescent probe bolus 602A and 602B and the time between each fluorescent probe bolus 602A and 602B may be predetermined. The plurality of fluorescent probes 602 may be configured to flow with the fluid in the lumen. The opening into lumen 34 and/or 54 may be upstream of a sensor, e.g., sensor 20 and/or fluorescence sensor 601, by a distance sufficient to allow the fluorescence probes of each of the boluses to disperse, yet each bolus may remain separated such that the fluorescence probes of one bolus do not intermix or overlap with the fluorescence probes of a preceding and/or subsequent bolus.

Processing circuitry 500 may control light source 604 to emit light 606 to expose fluorescent probes 602 within fluid 600 to light 606 in lumen 34 and/or 54 and thereby stimulate a fluorescence response from the plurality of fluorescent probes 602 (704). In some examples, fluorescence sensor 601 may be a stand-alone sensor having its own processing circuitry to control light source 604 to emit light 606 onto fluorescent probes 602 and to control light detector 610 to detect fluorescent light 616 that is emitted from fluorescent probes 602 in fluid 600 in lumen 34 and/or 54. In some examples, processing circuitry 500 may control light source 604 to emit excitation light 606 in a particular range of wavelengths corresponding to an excitation spectrum of the fluorescence material of fluorescent probes 602.

Light detector 610 may detect fluorescent light 616 from fluorescent probes 602 (706). In some examples, the fluorescent light 616 is indicative of a composition of fluid 600, for example, an amount of oxygen and a flow rate of fluid 600. In some examples, lens 614 may focus emitted light 606 through lens 614, e.g., to fluorescent probes 602. Additionally, or alternatively, lens 614 may also focus fluorescent light 616 from fluorescent probes 602 to light detector 610.

Processing circuitry 500 may determine an amount oxygen in fluid 600 within lumen 34 and/or 54 based on the detected fluorescence, e.g., based on FLT ($T_f$) (708). The greater the amount of oxygen present the lower the amount of fluorescent light 616 detected and the lower the amount of oxygen the higher the amount of fluorescent light 616 detected. For example, in some instances, processing circuitry 500 may determine a concentration of oxygen in fluid 600. Processing circuitry 500 may continually monitor light detector 610 sensing the FLT ($T_f$). Based upon $T_f$ processing circuitry may utilize a lookup table or an algorithm to determine an oxygen level within lumen 34 and/or 54. Further, processing circuitry 500 may determine an oxygen level at a specific point in time, or a running average of oxygen amount or even determine a trend of oxygen with lumen 34 and/or 54 over time.

As described above, processing circuitry 500 may determine a temperature of fluid 600 within lumen 34 and/or 54 as part of the determination of the oxygen in fluid 600. Fluorescence material may be temperature-dependent and to obtain a more accurate oxygen measurement the temperature of fluid 600 may be useful in calibrating the oxygen measurement. Processing circuitry 500 may use the temperature data collected from any of a number of data sources, for example, temperature sensors, an estimated temperature based on a patient's body temperature, another sensor coupled to external device 24 or a temperature inputted by a user at user interface 504. Processing circuitry 500 may use the temperature data to input into, e.g., an algorithm or a look up table to calibrate the oxygen calculation based on temperature of fluid 600 in combination with the rate of fluorescence decay detected by light detector 610.

Processing circuitry 500 may determine a flow rate of fluid 600 within lumen 34 and/or 54 based on the detected fluorescence from fluorescent probe boluses (708). In some examples, fluorescence sensor 601 may illuminate each fluorescent probe bolus 602A and 602B with excitation light 606, detect fluorescent light 616 from each of fluorescent probe bolus 602A and 602B after excitation, and processing circuitry may receive data from fluorescence sensor 601 corresponding to the detected fluorescent light 616 and/or FLT data. Processing circuitry may determine a flow rate based on a time duration of the detected fluorescence of one or more of fluorescent probe boluses and/or a time between detecting the fluorescence of individual boluses.

Any suitable technique may be employed by processing circuitry 500 to determine the level of oxygen in fluid 600 based on fluorescent light 616 detected by light detector 610. In some examples, processing circuitry 500 may reference a look up table in memory 502 to determine the oxygen level within fluid 600 based upon the detected fluorescence (e.g., alone or in combination with the determined temperature and determined flow rate). In some examples, processing circuitry 500 may execute an algorithm on memory 502 which calculates the oxygen level based upon fluorescent light 616 detected and, in some examples, the determined temperature and/or flow rate of fluid 600. In some examples, processing circuitry 500 may reference a lookup table stored in memory 619, memory 502 or memory 19. The lookup table may have a correlation for a specific fluorescence material and what the fluorescence material's fluorescence time ($T_f$) is based upon a determined temperature of fluid 600. Based upon the temperature of fluid 600, the flow rate, and the fluorescence time ($T_f$) sensed by light detector 610 a lookup table may provide a corresponding oxygen level of fluid 600 based on the known variables. In another example, a lookup table may be implemented in algorithmic form where the variables are inputted into the algorithm by processing circuitry 500 and an oxygen level is presented in display form on user interface 504 and/or through an audible form by a speaker on external device 24. In some examples, an alarm may be implemented through user interface 504 visually and/or audibly through a speaker if the oxygen level deviated outside of an upper or lower threshold. In another example, processing circuitry 500 may execute software 508 to perform the oxygen level determination based upon fluorescence time ($T_f$) and/or temperature and flow rate.

Figure 8:
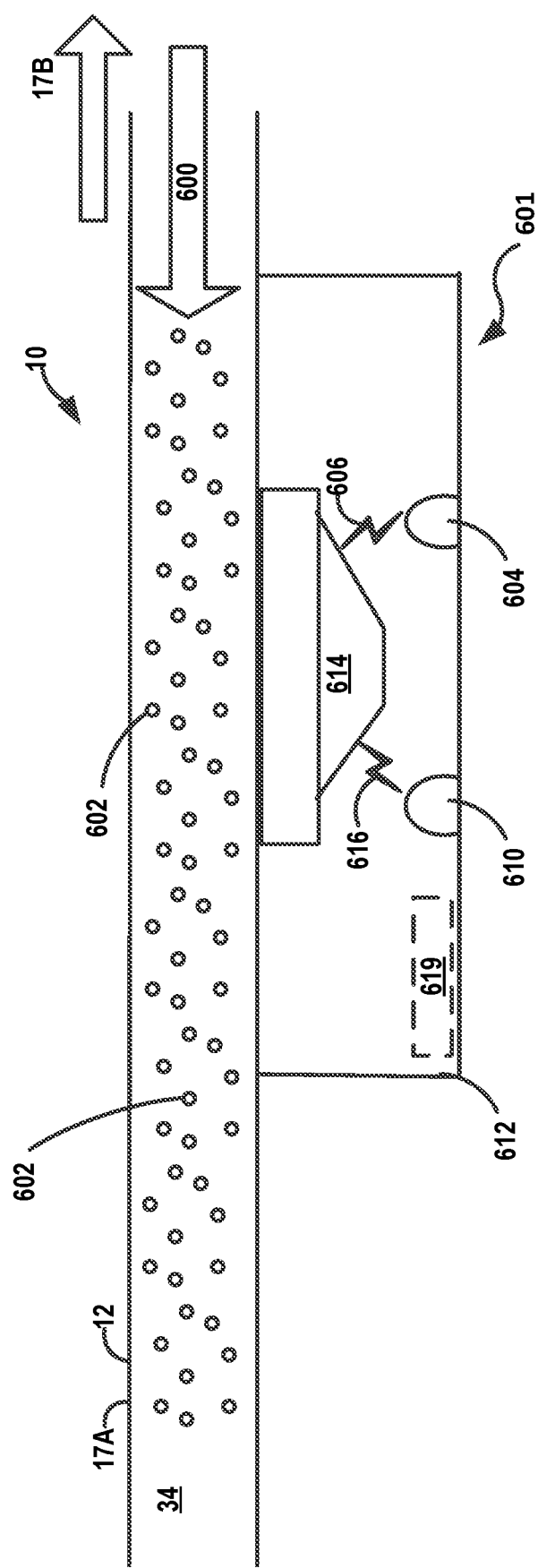
FIG. 8 is a diagram illustrating an example sensor used with a medical device according to the techniques of this disclosure.

FIG. 8 is a diagram illustrating an example fluorescence sensor 601 used with a medical device 10 and/or a medical device 50, according to the techniques of this disclosure. Fluorescence sensor 601 illustrated in FIG. 8 may be substantially similar to fluorescence sensor 601 as illustrated and described above with respect to FIG. 6. The example illustrated in FIG. 8 may be substantially similar to the example of FIG. 6, with the difference that the fluorescent probes 602 are released continuously rather than as discrete boluses.

In the example shown, fluorescent probes 602 are injected, released, introduced, etc., into fluid 600 upstream of fluorescence sensor 601 in a continuous manner, and may flow with fluid 600. Fluorescent probes 602 may be released for a predetermined amount of time at a predetermined rate and/or volume of fluorescent probes released per time. Fluorescent probes 602 may be configured to disperse within lumen 34 (or lumen 54) in both a longitudinal direction along lumen 34 and/or lumen 54 and the radial direction of lumen 34 and/or 54. In some examples, opening 44 (FIGS. 1 and 3) may be configured, individually or in combination with fluorescent probes 602, to release fluorescent probes 602 such that the fluorescent probes 602 disperse by a predetermined amount by the time they flow to the region and/or location along the length of lumen 34 and/or 54 of fluorescence sensor 601. In some examples, fluorescence sensor 601 is configured to sense oxygen in fluid 600 (e.g., oxygen concentration) using a FLT and fluorescent probes 602 released in a continuous manner.

Medical device 10 and/or 50 may be configured to determine a flow rate of fluid 600 based on a continuous release of fluorescent probes 602 into lumen 34 and/or 54. In some examples, probe tank 40 may inject the one or more probes into fluid 600 in a continuous manner. Fluorescence sensor 601 may illuminate the fluorescent probes 602 with excitation light 606 and capture a sequence of images of fluorescent probes 602 as they emit fluorescent light and flow with fluid 600.

In some examples, fluorescence sensor 601 may be configured to detect an image of the fluorescence of the plurality of fluorescing microbeads which may approximate a dispersion of a plurality of point-like discrete light sources in a volume and may be analogous to a speckle field, such as used with speckle contrast imaging and/or decorrelation speckle imaging. Sensor 601 may detect and/or capture one or more images the point-like fluorescent light sources comprising fluorescing microbeads, and processing circuitry may be configured to quantify the motion of the fluorescing microbeads to calculate a flow rate of the fluid within the lumen, as further described below.

Figure 9:
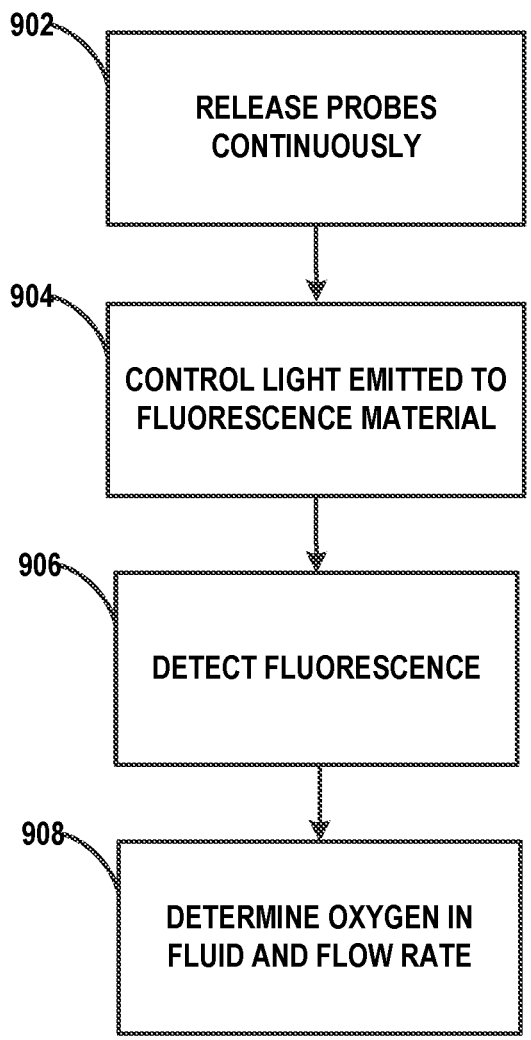
FIG. 9 is a flow diagram illustrating an example technique for monitoring or otherwise sensing oxygen and a flow rate of a fluid within a lumen using the sensor of FIG. 8 according to the techniques of this disclosure.

FIG. 9 is a flow diagram illustrating an example technique for monitoring or otherwise sensing oxygen and a flow rate of a fluid within a lumen, according to techniques of this disclosure.

A plurality of fluorescent probes 602 may be injected in a continuous manner into a fluid flowing in a lumen of elongated body 12 and/or 62 (902). For example, a probe tank may be fluidically connected to lumen 34 and/or 54 via a probe conduit and an opening into lumen 34 and/or 54. Processing circuitry may cause fluorescent probes 602 to be released from probe tank 40 into lumen 34 and/or 54 (e.g., via probe conduit 42) for a predetermined amount of time at a predetermined rate of release, e.g., an amount of fluorescent probes 602 per time. The plurality of fluorescent probes 602 may be configured to flow with the fluid in the lumen. The opening into lumen 34 and/or 54 may be upstream of a sensor, e.g., sensor 20 and/or fluorescence sensor 601, by a distance sufficient to allow fluorescence probes 602 to disperse within fluid 600 as fluid 600 and fluorescent probes 602 flow along elongated body 12 and/or 62.

Processing circuitry 500 may control light source 604 to emit light 606 to expose fluorescent probes 602 within fluid 600 to light 606 in lumen 34 and/or 54 and thereby stimulate a fluorescence response from the plurality of fluorescent probes 602 (904). In some examples, fluorescence sensor 601 may be a stand-alone sensor having its own processing circuitry to control light source 604 to emit light 606 onto fluorescent probes 602 and to control light detector 610 to detect fluorescent light 616 that is emitted from fluorescent probes 602 in fluid 600 in lumen 34 and/or 54.

Light detector 610 may detect fluorescent light 616 from fluorescent probes 602 (906). In some examples, the fluorescent light 616 is indicative of a composition of fluid 600, for example, an amount of oxygen and a flow rate of fluid 600. In some examples, lens 614 may focus emitted light 606 through lens 614, e.g., to fluorescent probes 602.

Additionally, or alternatively, lens 614 may also focus fluorescent light 616 from fluorescent probes 602 to light detector 610.

Processing circuitry 500 may determine an amount oxygen in fluid 600 within lumen 34 and/or 54 based on the detected fluorescence, e.g., based on FLT ($T_f$) (908). The greater the amount of oxygen present the lower the amount of fluorescent light 616 detected and the lower the amount of oxygen the higher the amount of fluorescent light 616 detected. For example, in some instances, processing circuitry 500 may determine a concentration of oxygen in fluid 600. Processing circuitry 500 may continually monitor light detector 610 sensing the FLT ($T_f$). Based upon $T_f$ processing circuitry may utilize a lookup table or an algorithm to determine an oxygen level within lumen 34 and/or 54. Further, processing circuitry 500 may determine an oxygen level at a specific point in time, or a running average of oxygen amount or even determine a trend of oxygen with lumen 34 and/or 54 over time.

As described above, processing circuitry 500 may determine a temperature of fluid 600 within lumen 34 and/or 54 as part of the determination of the oxygen in fluid 600. Fluorescence material may be temperature-dependent and to obtain a more accurate oxygen measurement the temperature of fluid 600 may be useful in calibrating the oxygen measurement. Processing circuitry 500 may use the temperature data collected from any of a number of data sources, for example, temperature sensors, an estimated temperature based on a patient's body temperature, another sensor coupled to external device 24 or a temperature inputted by a user at user interface 504. Processing circuitry 500 may use the temperature data to input into, e.g., an algorithm or a look up table to calibrate the oxygen calculation based on temperature of fluid 600 in combination with the rate of fluorescence decay detected by light detector 610.

Processing circuitry 500 may determine a flow rate of fluid 600 within lumen 34 and/or 54 based on the detected fluorescence (808). For example, light detector 610 may be a single detector, or may comprise an arrangement of a plurality of detecting elements configured to capture one or more images, such as an array of detector pixels of a camera. In some examples, fluorescence sensor 601 may capture a sequence of images of fluorescent probes 602 as they emit fluorescent light 616 (e.g., after excitation via light 606) and flow with fluid 600. Processing circuitry 500 may determine a flow rate of fluid 600 based on the sequence of images.

In some examples, fluorescence sensor 601 may be configured to a flow rate of fluid 600 using a technique analogous to speckle contrast imaging. The method of speckle contrast imaging takes advantage of an interference pattern formed when coherent light scatters randomly in a sample media. In some examples, single-wavelength light may be used to create a speckle pattern and/or speckle field. For example, light including multiple wavelengths and/or a range of wavelengths may create a plurality of overlapping speckle patterns that may "washout." This overlapping speckle pattern may significantly reduce the contrast of the overall interference pattern and may reduce and/or eliminate the speckle field. In some examples, light including a substantially narrow range of wavelengths may be used to create a speckle pattern and/or speckle field, e.g., light including a range of wavelengths ($\Delta\lambda$) less than about 5 nm, $\Delta\lambda$, less than about 2 nm, $\Delta\lambda$, less than about 1 nm, or any DL wavelength range suitable for creating a speckle pattern and/or speckle field.

The so-called speckle pattern comprises a plurality of bright and dark regions that is imaged onto a detector and/or an image sensor, e.g., a spatial contrast pattern. If the scattering objects are in motion, the speckle pattern will fluctuate during the exposure time of the image sensor, which will cause a blurring of the pattern. Similarly, a plurality of fluorescent probes 602 comprise a plurality of bright and dark regions within lumen 34 and/or 54 which may be imaged by sensor 601. If the fluorescent probes are in motion, the pattern will fluctuate during the exposure time of the image sensor, which will cause a blurring of the pattern. For a given camera exposure, faster fluctuations induce more blurring. One measure of the "blur" in a speckle image is commonly referred to as the speckle contrast, and is conventionally defined as:

$$K = \sigma/<I>$$

where $\sigma$ is the standard deviation and $<I>$ is the mean of N pixel intensities from the image sensor. Other measures of contrast can be used as well, with contrast being defined generally as any measure of disparity, difference, or distinction between values of multiple pixel elements of the image sensor, and/or the evolution of a single pixel element over time. Non-limiting examples include statistical properties of the spatial or temporal contrast, such as the speckle flow index (defined as $k0/K^2$ where K is the speckle contrast as described herein and k0 is a constant), standard deviation from mean or median, difference metrics such as mean percent difference (e.g., between pixels of the image sensor), potential-well fill time difference, gradient between pixels, metrics of comparisons between subregions such as subtraction, the magnitude of fluctuation in the pixel intensities over time, reduction of the pixels to local binary patterns or local ternary patterns, etc. An autocorrelation performed on the signal generated by a single pixel over a period of time may quantify the temporal decorrelation in detected light intensity as a result of the motion of the moving light scattering particles. In some examples, the spatial contrast pattern (e.g., from the plurality of fluorescent probes 602) can be related to the autocorrelation time of the image of the spatial contrast image, which can then be related to the mean square displacement (e.g. flow speed or diffusion) of the moving objects, e.g., fluorescent probes 602, in the fluid. In general, a relatively high contrast speckle pattern will produce higher values of K and a more blurry pattern will produce lower values of K. The rate of movement (e.g., flow) within a sample can then be related to the contrast, which can be computed either through analytic or empirical means. It should also be noted that temporal calculations of K, where contrast is derived from a single optical detection element over time can be used interchangeably with spatial computations of contrast. Temporal calculations of K depend on the arithmetic comparison of different intensity values within a single optical element over a period of time. In this case, multiple values for a single optical element collected over a sequence of time are compared to one another, as opposed to the comparison of values of an optical detection element to that of its surrounding neighbors at the same moment in time. While temporal calculations of K involve the comparison of a single optical element to itself, by comparing different values detected over time, the ultimate calculation of K can and often involves multiple optical detection elements. Additionally, combinations of spatial and temporal calculations of contrast may also be used without a loss of generality. In some embodiments, the rate of movement may be determined as the speed, or average speed (e.g., m/s), of the moving light scatterers and/or emitters within a sample. The flow rate may be a measure of the volume of fluid (e.g., urine) transported per unit of time (i.e. volumetric flow) and may be represented in any suitable units (e.g., cm3/s). In some embodiments, the flow rate may be determined as a measure of volumetric flux (e.g., m3·s-1·m-2) through, for example, a catheter.

In some examples, fluorescence sensor 601 may be configured to a flow rate of fluid 600 using speckle decorrelation. For example, light source 604 may be a coherent and substantially monochromatic light source, such as a laser light source, configured to illuminate fluorescent probes 602 in fluid 600. Fluorescent probes 602 may reflect and/or scatter the coherent and substantially monochromatic light. The reflecting and/or scattering fluorescent probes may create a speckle pattern and/or speckle field, and speckle decorrelation may be used to determine a flow rate of the fluid based on the speckle pattern and/or fluctuations of the speckle pattern.

Any suitable technique may be employed by processing circuitry 500 to determine the level of oxygen and flow rate of fluid 600 based on fluorescent light 616 detected by light detector 610. In some examples, the level of oxygen and flow rate of the fluid may be detected and/or determined substantially simultaneously using one or more techniques, e.g., FLT and contrast imaging using the same sensor 601 and same plurality of fluorescent probes 602.

In some examples, processing circuitry 500 may reference a look up table in memory 502 to determine the oxygen level within fluid 600 based upon the detected fluorescence (e.g., alone or in combination with the determined temperature and determined flow rate). In some examples, processing circuitry 500 may execute an algorithm on memory 502 which calculates the oxygen level based upon fluorescent light 616 detected and, in some examples, the determined temperature and/or flow rate of fluid 600. In some examples, processing circuitry 500 may reference a lookup table stored in memory 619, memory 502 or memory 19. The lookup table may have a correlation for a specific fluorescence material and what the fluorescence material's fluorescence time ($T_f$) is based upon a determined temperature of fluid 600. Based upon the temperature of fluid 600, the flow rate, and the fluorescence time ($T_f$) sensed by light detector 610 a lookup table may provide a corresponding oxygen level of fluid 600 based on the known variables. In another example, a lookup table may be implemented in algorithmic form where the variables are inputted into the algorithm by processing circuitry 500 and an oxygen level is presented in display form on user interface 504 and/or through an audible form by a speaker on external device 24. In some examples, an alarm may be implemented through user interface 504 visually and/or audibly through a speaker if the oxygen level deviated outside of an upper or lower threshold. In another example, processing circuitry 500 may execute software 508 to perform the oxygen level determination based upon fluorescence time ($T_f$) and/or temperature and flow rate.

Various examples have been described. These and other examples are within the scope of the following claims. For purposes of this disclosure, the operations shown FIGS. 6, 8, 10, 11 and 12 do not need to be executed in the manner suggested by the illustrations and, unless specifically stated so, may be executed in any order. Further, the term substantially is to be given its standard definition of to a great or significant extent or for the most part; essentially.

The following is a non-limiting list of examples that are in accordance with one or more techniques of this disclosure.

Example 1: A device includes an elongated body defining a lumen, the elongated body comprising a proximal portion and a distal portion; and one or more sensors configured to: stimulate a fluorescence response from one or more fluorescent probes released into a fluid and flowing with the fluid through the lumen; and detect the fluorescence response, wherein the fluorescence response is indicative of a composition of the fluid.

Example 2: The device of example 1, wherein the one or more sensors comprise: a light source configured to emit light into the fluid flowing in the lumen to expose the one or more fluorescent probes to the emitted light; and a light detector configured to detect the fluorescence response of the one or more fluorescent probes.

Example 3: The device of example 2, wherein the one or more fluorescent probes comprise a plurality of fluorescent microbeads configured to disperse within the fluid, and wherein the plurality of fluorescent microbeads comprise a plurality of microbeads and a fluorescence material coated onto the plurality of microbeads.

Example 4: The device of example 3, further comprising an opening in the elongated body in fluid communication with the lumen, wherein the opening is configured to receive the plurality of fluorescent microbeads.

Example 5: The device of example 4, wherein the opening is located a distance upstream from the light source and the light detector, the distance greater than a length required to disperse the fluorescent microbeads within the fluid.

Example 6: The device of any of examples 1 to 5, further comprising a computing device configured to determine at least one of an amount of oxygen or a concentration of oxygen in the fluid within the lumen based on the fluorescence response.

Example 7: The device of example 6, wherein the computing device is further configured to determine a flow rate of the fluid within the lumen based on the detected fluorescence.

Example 8: The device of example 7, wherein the computing device is configured to determine the flow rate of the fluid within the lumen based on: a duration of the detected fluorescence response of at least two discrete boluses of fluorescent microbeads; and a time delay between detection of the detected fluorescence response of the at least two discrete boluses of fluorescent microbeads.

Example 9: The device of example 7, wherein the computing device is configured to determine the flow rate of the fluid within the lumen based on at least one of contrast imaging of fluorescent microbeads, speckle contrast imaging of fluorescent microbeads, or speckle decorrelation.

Example 10: The device of any of examples 1 to 9, wherein the elongated body comprises a material that is substantially non-permeable to oxygen.

Example 11: The device of example 10, wherein the material comprises at least one of nylon, polyethylene terephthalate (PET), or polytetrafluoroethylene (PTFE).

Example 12: The device of any of examples 1 to 11, wherein the elongated body comprises a catheter.

Example 13: The device of any of examples 1 to 12, wherein the elongated body is configured to attach to a catheter such that the lumen is in fluid communication with a lumen of the catheter.

Example 14: A method includes injecting one or more fluorescent probes into a fluid flowing in a lumen defined by an elongated body comprising a proximal portion and a distal portion, the one or more fluorescent probes configured to flow with the fluid in the lumen; stimulating a fluorescence response from the one or more fluorescent probes in the fluid flowing through the lumen; and detecting the fluorescence response, wherein the fluorescence response is indicative of a composition of the fluid.

Example 15: The method of example 14, further comprising determining, based on the fluorescence response, at least one of an amount of oxygen or a concentration of oxygen in the fluid.

Example 16: The method of example 14 or 15, wherein stimulating the one or more fluorescent probes comprises causing a light source to emit light into the fluid flowing in the lumen to expose the one or more fluorescent probes to the emitted light, and wherein detecting the fluorescence response comprises detecting, by a light detector, the fluorescence response of the fluorescence material.

Example 17: The method of example 16, further comprising determining, based on the fluorescence response, a flow rate of the fluid.

Example 18: The method of example 17, wherein injecting the one or more fluorescent probes into the fluid comprises injecting a plurality of discrete boluses of fluorescent microbeads into the fluid upstream of the light source at a predetermined time delay between each of the plurality of discrete boluses, wherein each of the plurality of discrete boluses includes a predetermined volume of fluorescent microbeads, and wherein determining the flow rate of the fluid comprises determining the flow rate of the fluid based on: a duration of the detected fluorescence response of at least two discrete boluses of fluorescent microbeads; and a time delay between detection of the detected fluorescence response of the at least two discrete boluses of fluorescent microbeads.

Example 19: The method of example 17, wherein injecting the one or more fluorescent probes into the fluid comprises continuously injecting a plurality of fluorescent microbeads into the fluid upstream of the light source over a period of time, and wherein determining the flow rate of the fluid comprises determining the flow rate of the fluid based on contrast imaging of the fluorescence response of the plurality of fluorescent microbeads.

Example 20: A system includes an elongated body defining a lumen, the elongated body comprising a proximal portion and a distal portion; a plurality of fluorescent microbeads configured to flow through the lumen, wherein the plurality of fluorescent microbeads is configured to fluoresce in response to light; and one or more sensors in photonic communication with the lumen, the one or more sensors configured to: stimulate a fluorescence response from the plurality of fluorescent microbeads in the fluid flowing through the lumen; and detect the fluorescence response from the plurality of fluorescent microbeads, wherein the fluorescence response is indicative of a composition of the fluid.

Example 21: The system of example 20, wherein the one or more sensors further comprise: a light source configured to emit light to expose the plurality of fluorescent microbeads to the emitted light, wherein the plurality of fluorescent microbeads is configured to fluoresce when exposed to the light; and a light detector configured to detect the fluorescence response of the plurality of fluorescent microbeads.

Example 22: The system of example 20 or 21, further comprising a fluorescent microbead supply configured to release the plurality of fluorescent microbeads into the fluid upstream from the light source.

Example 23: The system of example 22, wherein the fluorescent microbead supply is configured to deliver a plurality of discrete boluses of fluorescent microbeads to the fluid with a predetermined time delay between each of the plurality of boluses, and wherein each of the plurality of discrete boluses includes a predetermined volume of the fluorescent microbeads.

Example 24: The system of example 22 or 23, wherein the fluorescent microbead supply is configured to continuously deliver the plurality of fluorescent microbeads to the fluid over a period of time.

Example 25: The system of any of examples 20 to 24, further comprising a computing device configured to: determine, based on the fluorescence response, at least one of an amount of oxygen or a concentration of oxygen in the fluid within the lumen; and determine, based on the fluorescence response, a flow rate of the fluid within the lumen.

Example 26: The system of any of examples 20 to 25, wherein the elongated body comprises a material that is substantially non-permeable to oxygen.

Example 27: The system of any of examples 20 to 26, wherein the elongated body is configured to be attached to a catheter supplying the fluid to the lumen.

Example 28: The system of any of examples 20 to 27, wherein the plurality of fluorescent microbeads is configured to interact with oxygen in the fluid and emit the fluorescence response based on the interactions with the oxygen in the fluid.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements.

What is claimed is:

1. A device comprising:
 an elongated body defining a lumen, the elongated body comprising:
  a proximal portion and a distal portion; and
  an opening in fluid communication with the lumen, wherein the opening is configured to receive a plurality of microbeads coated with a fluorescent material; and
 one or more sensors configured to:

stimulate a fluorescence response from the plurality of microbeads released into a fluid and flowing with the fluid through the lumen; and detect the fluorescence response, wherein the fluorescence response is indicative of a composition of the fluid, wherein the one or more sensors comprise:
a light source configured to emit light into the fluid flowing in the lumen to expose the plurality of microbeads to the emitted light; and
a light detector configured to detect the fluorescence response of the plurality of microbeads.

2. The device of claim 1, wherein the opening is located a distance upstream from the light source and the light detector, the distance greater than a length required to disperse the fluorescent microbeads within the fluid.

3. The device of claim 1, further comprising a computing device configured to determine at least one of an amount of oxygen or a concentration of oxygen in the fluid within the lumen based on the fluorescence response.

4. The device of claim 3, wherein the computing device is further configured to determine a flow rate of the fluid within the lumen based on the detected fluorescence.

5. The device of claim 4, wherein the computing device is configured to determine the flow rate of the fluid within the lumen based on:
a duration of the detected fluorescence response of at least two discrete boluses of fluorescent microbeads of the plurality of fluorescent microbeads; and
a time delay between detection of the detected fluorescence response of the at least two discrete boluses of fluorescent microbeads.

6. The device of claim 4, wherein the computing device is configured to determine the flow rate of the fluid within the lumen based on at least one of contrast imaging of fluorescent microbeads, speckle contrast imaging of fluorescent microbeads, or speckle decorrelation.

7. The device of claim 1, wherein the elongated body comprises a material that is substantially non-permeable to oxygen.

8. The device of claim 7, wherein the material comprises at least one of nylon, polyethylene terephthalate (PET), or polytetrafluoroethylene (PTFE).

9. The device of claim 1, wherein the elongated body comprises a catheter.

10. The device of claim 1, wherein the elongated body is configured to attach to a catheter such that the lumen is in fluid communication with a lumen of the catheter.

11. A method comprising:
injecting a plurality of fluorescent microbeads into a fluid flowing in a lumen defined by an elongated body comprising a proximal portion and a distal portion, wherein the plurality of fluorescent microbeads are coated with a fluorescent material and are configured to flow with the fluid in the lumen;
stimulating a fluorescence response from the plurality of fluorescent microbeads in the fluid flowing through the lumen, wherein stimulating the plurality of fluorescent microbeads comprises causing a light source to emit light into the fluid flowing in the lumen to expose the plurality of fluorescent microbeads to the emitted light; and
detecting, via a light detector, the fluorescence response from the plurality of fluorescent microbeads, wherein the fluorescence response is indicative of a composition of the fluid.

12. The method of claim 11, further comprising determining, based on the fluorescence response, at least one of an amount of oxygen or a concentration of oxygen in the fluid.

13. The method of claim 11,
wherein detecting the fluorescence response comprises detecting, by the light detector, the fluorescence response of the fluorescence material.

14. The method of claim 13, further comprising determining, based on the fluorescence response, a flow rate of the fluid.

15. The method of claim 14,
wherein injecting the plurality of fluorescent microbeads into the fluid comprises injecting a plurality of discrete boluses of the plurality of fluorescent microbeads into the fluid upstream of the light source at a predetermined time delay between each of the plurality of discrete boluses,
wherein each of the plurality of discrete boluses includes a predetermined volume of the plurality of fluorescent microbeads, and
wherein determining the flow rate of the fluid comprises determining the flow rate of the fluid based on:
a duration of the detected fluorescence response of at least two discrete boluses of fluorescent microbeads of the plurality of discrete boluses; and
a time delay between detection of the detected fluorescence response of the at least two discrete boluses of fluorescent microbeads.

16. The method of claim 14,
wherein injecting the plurality of fluorescent microbeads into the fluid comprises continuously injecting the plurality of fluorescent microbeads into the fluid upstream of the light source over a period of time, and
wherein determining the flow rate of the fluid comprises determining the flow rate of the fluid based on contrast imaging of the fluorescence response of the plurality of fluorescent microbeads.

17. A system comprising:
an elongated body defining a lumen, the elongated body comprising a proximal portion and a distal portion;
a plurality of fluorescent microbeads configured to flow through the lumen, wherein the plurality of fluorescent microbeads is configured to fluoresce in response to light; and
one or more sensors in photonic communication with the lumen, the one or more sensors configured to:
stimulate a fluorescence response from the plurality of fluorescent microbeads in the fluid flowing through the lumen;
detect the fluorescence response from the plurality of fluorescent microbeads, wherein the fluorescence response is indicative of a composition of the fluid,
wherein the one or more sensors comprise:
a light source configured to emit light to expose the plurality of fluorescent microbeads to the emitted light, wherein the plurality of fluorescent microbeads is configured to fluoresce when exposed to the light; and
a light detector configured to detect the fluorescence response of the plurality of fluorescent microbeads; and
a probe tank configured to release the plurality of fluorescent microbeads into the fluid upstream of the light source, wherein the probe tank is configured to deliver a plurality of discrete boluses of fluorescent microbeads to the fluid with a predetermined time delay between each of the plurality of boluses, and wherein each of the plurality of discrete boluses includes a predetermined volume of the fluorescent microbeads.

18. The system of claim 17, wherein the probe tank is configured to continuously deliver the plurality of fluorescent microbeads to the fluid over a period of time.

19. The system of claim 17, further comprising a computing device configured to:
   determine, based on the fluorescence response, at least one of an amount of oxygen or a concentration of oxygen in the fluid within the lumen; and
   determine, based on the fluorescence response, a flow rate of the fluid within the lumen.

20. The system of claim 17, wherein the elongated body comprises a material that is substantially non-permeable to oxygen.

21. The system of claim 17, wherein the elongated body is configured to be attached to a catheter supplying the fluid to the lumen.

22. The system of claim 17, wherein the plurality of fluorescent microbeads is configured to interact with oxygen in the fluid and emit the fluorescence response based on the interactions with the oxygen in the fluid.

23. A device comprising:
an elongated body defining a lumen, the elongated body comprising a proximal portion and a distal portion;
one or more sensors configured to:
   stimulate a fluorescence response from one or more fluorescent probes released into a fluid and flowing with the fluid through the lumen; and
   detect the fluorescence response, wherein the fluorescence response is indicative of a composition of the fluid; and
a computing device configured to determine:
   at least one of an amount of oxygen or a concentration of oxygen in the fluid within the lumen based on the fluorescence response; and
   a flow rate of the fluid within the lumen based on:
      a duration of the detected fluorescence response of at least two discrete boluses of fluorescent microbeads; and
      a time delay between detection of the detected fluorescence response of the at least two discrete boluses of fluorescent microbeads.

* * * * *